(12) United States Patent
Kim et al.

(10) Patent No.: US 8,724,117 B2
(45) Date of Patent: May 13, 2014

(54) SYSTEM FOR MEASURING ELECTRO-OPTIC COEFFICIENT BY USING INTERFERENCE FRINGE MEASUREMENT, AND METHOD OF MEASURING ELECTRO-OPTIC COEFFICIENT BY USING THE SYSTEM

(75) Inventors: Kyong-Hon Kim, Yeonsu-gu (KR); Seoung-Hun Lee, Namdong-gu (KR); Seung-Hwan Kim, Nam-gu (KR); El-Hang Lee, Goyang-si (KR)

(73) Assignee: Inha Industry Partnership Institute, Incheon (KR)

( * ) Notice: Subject to any disclaimer, the term of this patent is extended or adjusted under 35 U.S.C. 154(b) by 895 days.

(21) Appl. No.: 12/779,236

(22) Filed: May 13, 2010

(65) Prior Publication Data

US 2010/0290055 A1  Nov. 18, 2010

(30) Foreign Application Priority Data

May 13, 2009 (KR) .................. 10-2009-0041827

(51) Int. Cl.
*G01B 9/02* (2006.01)
(52) U.S. Cl.
USPC ......................................... 356/517; 356/491
(58) Field of Classification Search
USPC ......... 356/450, 451, 453, 456, 491, 495, 517, 356/515, 481
See application file for complete search history.

(56) References Cited

U.S. PATENT DOCUMENTS

| | | | |
|---|---|---|---|
| 6,377,349 B1* | 4/2002 | Fercher | 356/497 |
| 6,765,680 B2* | 7/2004 | Carr et al. | 356/510 |

* cited by examiner

*Primary Examiner* — Hwa Lee
(74) *Attorney, Agent, or Firm* — Sherr & Jiang, PLLC

(57) ABSTRACT

Measuring of an electro-optic coefficient and a thermo-optic coefficient of an optical device and an optical material, and more specifically, to measurement systems and methods of evaluating the electro-optic and thermo-optic coefficients by using interference fringe measurement techniques, wherein those optical characteristics can be precisely measured over a wide wavelength intended without using a complicated measuring equipment. The system for measuring an electro-optic coefficient includes: a light source for outputting an optical beam of multi-wavelengths, an optical interferometer including an optical beam splitter for dividing the optical beam received from the light source into two separate beams, a reference arm for receiving any one of the divided optical beams, a sample arm for receiving the other of the divided optical beams and applying a voltage to an optical sample to be measured by being connected to the optical sample, and an optical beam combiner for combining and mutually interfering optical beams that are output through the reference arm and the sample arm, and an optical spectrum analyzing device for receiving the mutually interfered optical beam from the optical interferometer and analyzing a spectrum of the mutually interfered optical beam.

3 Claims, 17 Drawing Sheets

SYSTEM FOR MEASURING ELECTRO-OPTIC COEFFICIENT BY USING INTERFERENCE FRINGE MEASUREMENT, AND METHOD OF MEASURING ELECTRO-OPTIC COEFFICIENT BY USING THE SYSTEM

CROSS-REFERENCE TO RELATED PATENT APPLICATION

This application claims the benefit of Korean Patent Application No. 10-2009-0041827, filed on May 13, 2009, in the Korean Intellectual Property Office, the disclosure of which is incorporated herein in its entirety by reference.

BACKGROUND OF THE INVENTION

1. Field of the Invention

The present invention relates to measurement systems and methods of evaluating electro-optic (EO) coefficients and thermo-optic (TO) coefficients of optical devices or optical materials, more specifically, to measurement systems and methods of evaluating the electro-optic and thermo-optic coefficients by using interference fringe measurement techniques, wherein those optical characteristics can be precisely measured over a wide wavelength intended without using a complicated measuring equipment.

2. Description of the Related Art

Knowledge of the second-order nonlinear electro-optic coefficients and thermo-optic coefficients of optical materials or optical devices are important in realizing various optical functional devices these days.

The second-order nonlinear electro-optic coefficients are significantly related to optical device performance characteristics of electro-optic modulators, optical deflectors, second harmonic wave generators, wavelength converters, optical switches, optical parametric amplifiers, and quantum entangled optical signal generators, while the thermo-optic coefficients are related to optical device performance characteristics of optical switches, variable filters, variable optical attenuators, and optical modulators.

Thus, measurement of the second-order nonlinear electro-optic coefficients and thermo-optic coefficients of the optical materials or the optical devices is very important because they affect their device performance.

There are a number of conventional measurement methods of evaluating the second-order nonlinear coefficient, such as the Mach-Zehnder interferometer method using a single wavelength light source and a reference optical medium disclosed in K. Onuki, et al., J. Optical Society of America 62 (9), 1030-1032 (1972), and J. A. de Toro, et al., Opt. comm. 154, 23-27 (1998); a method of analyzing an index ellipsoid structure of a reflection-type single beam polarization interferometer of poled polymers disclosed in M. J. Shin, et al., J. Korean Phys. Soc. 31 (1) 99-103 (1997), C. C. Teng & H. T. Man, Appl. Phys. Lett., 56 (18) 1734-1736 (1990), C. J. Novotny, et al., Nano Lett. 8 (4) 1020-1025 (2008), and D. H. Park, et al., Opt. Express 14 (19), 8866-8884 (2006); a method of using interference fringes of transmitted beams after multiple reflection within a Fabry-Perot etalon shaped second-order nonlinear coefficient material disclosed in K. Takizawa and Y. Yokota, Opt. Review 13 (3), 161-167 (1982), and K. Yonekura, et al, Jap. J. Appl. Phys., 47 (7) 5503-5508 (2008); a method of measuring a phase change between two polarization beams caused by the birefringence of a second-order nonlinear material disclosed in Z. Shen, et al., Thin Solid Films 488, 40-44 (2005), H. Adachi, et al. Appl. Phys. Lett., 42 (10) 867-868 (1983), Y. Jeon and H. S. Kang, Opt. Review 14 (6), 373-375 (2007), K. Tada and M. Aoki: Jpn. J. Appl. Phys. 10 (8), 998-1001 (1971), A. Hou, et al., Opt. & Laser Technol. 39, 411-414 (2007), A. Grunnet-Jepsen, et al., J. Opt. Soc. Am. B 12 (5), 921-929 (1995), and K. Li, U.S. patent Ser. No. 10/139,857 (May 6, 2002); a method of using second harmonic wave generation in a second-order nonlinear material disclosed in R. C. Eckardt, et al., IEEE J. Quantum Electron. 26 (5), 922-933 (1990), and I. Shoji, et al., J. Opt. Soc. Am. B 16 (4), 620-624 (1999); a method of measuring a second-order nonlinear coefficient by using spatial distribution of an interferometer output beam of a Mach-Zehnder interferometer composed of bulk-type optics disclosed in H. P. Sardesai, et al., Appl. Opt. 33 (10), 1791-1794 (1994); and a method of measuring an output signal change of an optical waveguide-type Mach-Zehnder interferometer made of a second-order nonlinear material as a function of a applied modulation voltage disclosed in Y. Enami, et al., Nature Photonics, vol. 1, 180-185 (2007) & vol. 1, p. 423 (2007).

The Mach-Zehnder interferometer method using a single wavelength light source and a reference optical medium requires an optical modulator made of a standard and well known second-order nonlinear material, and has disadvantages of limited measurement of the electro-optic coefficient only at a single wavelength and a measurement accuracy limited at the maximum accuracy of the EO coefficient of reference material.

The method of analyzing an index ellipsoid structure of a reflection-type single beam polarization interferometer of poled polymers is a method of obtaining an electro-optic coefficient by preparing one side of a second-order nonlinear optical sample to be a reflective type and the other side to be a transmission type, and adjusting and measuring an angle of a light refracted and reflected within the sample with respect to an irradiated light of a single wavelength. However, in this method the second-order nonlinear optical sample needs to be specially fabricated according to its use, and the measured EO value may have a significant error depending on the angle measurement accuracy and data analysis.

The method of using interference fringes between a light beam directly passing through a Fabry-Perot etalon shaped second-order nonlinear material and transmitted beams after multiple reflections within the material sample uses a method of analyzing frequencies of electric signals generated from an optical detector when it detects modulated signals from the FP etalon shaped second-order nonlinear medium and then comparing their distributions of a Bessel function of the first kind and of the first order and of a Bessel function of the first kind and of the third order. However, this method requires quite complex signal processing steps.

The method of measuring a phase change between two polarization beams caused by the birefringence of a second-order nonlinear material requires adjustment of the polarization state of an input optical signal beam and precise measurement of the polarization states of the output optical signals from the nonlinear material sample, and results in determination of the refractive index of a low accuracy level.

According to the method of using second harmonic wave generation in a second-order nonlinear material, the absolute and a relative values of its second-order nonlinear optical coefficient may be obtained, but it may be difficult to have a phase matching condition for the second harmonic wave generation, and thus it is highly likely that an error may occur.

In the method of measuring the second-order nonlinear coefficient by using spatial distribution of an interferometer output beam of a Mach-Zehnder interferometer composed of bulk-type optics, it is difficult to accurately analyze 2-dimensional interference fringe distribution in a process of determining the nonlinear refractive index, and the same measurement procedures need to be repeated continuously over a desired wavelength range in steps of discrete single wavelength measurement.

Examples of the conventional method of measuring the thermo-optic coefficient include: a method of composing a Mach-Zehnder interferometer with a single wavelength light source disclosed in J. Mangin, P. Strimer and L. Lahlou-Kassi, Meas. Sci. Technol., vol. 4, 826-834 (1993); a method of using an interference fringe of a Fabry-Perot interferometer disclosed in W. J. Tropf and M. E. Thomas, Meas. Johns Hopkins APL Technical Digest, 19 (3), 293-298 (1998); a method of using a change of interference fringes according to rotation of a sample disclosed in S. De Nicola, et al., J. Opt. A: Pure Appl. Opt., 1, 702-705 (1999); a method of using a ring type resonator structure of a sample and a heterodyne optical detection disclosed in S. Chang, et al., Chinese J. Phys. 38 (3-1), 437-442 (2000), and C.-C. Hsu, et al., J. Appl. Phys., vol. 77 (7), 3399-3402 (1995); a method of using a Fizeau interference fringe of a thin sample disclosed in S. S. Bayya, et al., Appl. Opt., vol. 46 (32), 7889-7891 (2007), R. J. Harris, et al., Appl. Opt., vol. 16 (2), 436-438 (1977), and P. A. Williams, et al., Appl. Opt., vol. 35 (19), 3562-3569 (1996); a method of using a heating scheme on a sample and of detecting its TO effect with a prism coupler disclosed in Eun-ji Kim, Young-gyu Lee, Woo-hyuk Jang, Tae-hyung Lee (Samsung Electronics Co., Ltd), Korean Patent No. 10-0322128 (Jan. 14, 2002); a method of measuring waist sizes of a Gaussian optical beam penetrating a liquid or gel-type sample between micro double lenses disposed in L. Huang, et al., CLEO 2004, paper CThII1; and a method of measuring the minimum deviation angle of a penetrating beam through a prism-shaped sample disclosed in D. J. Gettemy, et al., IEEE J. Quantum Electron., 24 (11), 2231-2237 (1988), and B. Zysset, I. Biaggio. and P. Gunter, J. Opt. Soc. Am. B, 9 (3), 380-386 (1992).

In the method of composing a Mach-Zehnder interferometer with a single wavelength light source, Fizeau interference fringes are used together to measure thermal expansion coefficient simultaneously with the TO coefficient, but the measurement scheme is quite complicated and measures the thermo-optic coefficient only at a single wavelength.

In the method of using an interference fringe of a Febry-Perot interferometer an interference fringe spectrum transmitted from a solid etalon-shaped sample is fitted with a Sellmeier equation with suitable coefficients to obtain wavelength dependent refractive indices, and then thermo-optic coefficient is obtained from the refractive index change for various temperatures.

In the method of using a change of interference fringes according to rotation of a sample, a refractive index is calculated from a phase change of the interference fringes caused by rotation of an angle of a thin sample placed on one path of an interferometer. Then, the thermo-optic coefficient is also obtained by obtaining the refractive index change for various temperatures.

The method of using a ring type resonator structure of a sample and a heterodyne optical detection has a drawback because it requires a specially shaped sample so that a light beam propagates in its ring-shaped resonator, and a phase change measuring method with an electrical heterodyne detection scheme.

The method of using Fizeau interference fringes of a thin sample requires thermal expansion coefficient (TEC) measurement by using a conventional commercial TEC measurement method, and determine its thermo-optic coefficient by measuring phase changes of the Fizeau interference fringes formed by reflected beams from the front and rear surfaces of the sample as its temperature is varied. However, this method may be sensitive to vibration on the optical alignment of the bulk optical system under external environment changes.

The method of using a heating scheme on a sample and of detecting its TO effect with a prism coupler is basically based on conventional measurement scheme of the refractive index of an thin film sample, but is packaged with a thermoelectric device to change the temperature of the thin polymer sample.

The method of measuring waist sizes of a Gaussian optical beam penetrating a liquid or gel-type sample between micro double lenses requires use of a liquid or gel type sample only, and also has disadvantages of requiring an inconvenient heating scheme on the sample and of delivering a limited measurement accuracy of the TO coefficient of the sample caused by the measurement accuracy of the waist size of the penetrated optical beam.

The method of measuring the minimum deviation angle of a penetrating beam through a prism-shaped sample has also some drawbacks of requiring preparation of a sample in a prism shape and of limited validity of the method only for the cases that the sample has uniform thermo-optic and thermal expansion coefficients. A refractive index measured by using the method is accurate up to fourth digit after the decimal point, but this method is not accurate enough for the thermo-optic coefficient measurement because the TO coefficients of most materials are on the order of fifth or sixth digits after the decimal point.

SUMMARY OF THE INVENTION

The present invention provides fast and accurate measurement systems and methods of the electro-optic and thermo-optic coefficients of optical devices or optical materials over a wide wavelength range with a basic optical interferometer scheme and the samples of a simple form from measurement of the interference fringes measurement.

In order to achieve one of the goals of the present invention, a system for measuring an electro-optic coefficient by using interference fringe measurement is provided by including: a light source for outputting an optical beam of multi-wavelengths; an optical interferometer including an optical signal splitter for dividing the optical signal received from the light source into two separate beams, a reference arm receiving any one of the divided optical beams, a sample arm receiving the other beam and having an optical sample to be measured with a voltage applicable to it, and an optical beam combiner for combining the two beams, each passed through one of the reference and sample arms respectively, together to produce an interfered optical beam output; and an optical spectrum analyzing device for receiving the interfered optical beam from the optical interferometer and analyzing its spectrum characteristics.

In order to achieve another goal of the present invention, another system for measuring a thermo-optic coefficient by using interference fringe measurement is provided by including: a light source for outputting an optical beam of multi-wavelengths; an optical interferometer including an optical beam splitter for dividing the optical beam received from the light source into two separate beams, a reference arm for receiving any one of the divided optical beams, a sample arm for receiving the other beam and having an optical sample to be measured with a heater to control its temperature, and an optical beam combiner for combining the two beams, each passed through one of the reference and sample arms respectively, together to produce an interfered optical beam output;

and an optical spectrum analyzing device for receiving the interfered optical beam output from the optical interferometer and analyzing its spectrum characteristics.

In order to achieve another goal of the present invention, a method of measuring an electro-optic coefficient is provided by (1) using a light source for outputting an optical beam of multi-wavelengths, an optical interferometer for dividing the optical received from the light source into two separate beams, (2) supplying each of the two optical beams to a reference arm and a sample arm, respectively, having an optical sample to be measured on the sample arm, (3) combining the two beams, each passed through one of the reference and sample arms respectively, together to produce an interfered optical beam output, and an optical spectrum analyzing device for receiving the interfered optical beam output from the optical interferometer and analyzing its spectrum characteristics, and (4) including procedures composed of: (i) a process obtaining a reference frequency spectrum, directly or converting the wavelength into the frequency after measuring a wavelength spectrum, from the interferometer output while no voltage is applied to the optical sample; (ii) another process obtaining a normalized reference interference fringe spectrum by measuring a spectrum of the interferometer output when only one of the reference and sample arms is alternately blocked under no voltage is applied as in the case of the above reference frequency spectrum acquisition process, which corresponds to the measured spectrum of the other arm not blocked, and then by excluding this spectrum from the reference frequency spectrum obtained in the above process; (iii) a process calculating reference phase difference values from the above normalized reference interference fringe spectrum as a function of frequency change from a predetermined particular reference frequency; (iv) a process obtaining another frequency spectrum of the interference output with a sample voltage-on, either directly or by converting the wavelength into the frequency after measuring a wavelength spectrum, from the optical interferometer when a voltage is applied to the optical sample; (v) another process obtaining a normalized interference fringe spectrum of the interferometer with a sample voltage-on, by measuring a spectrum of the interferometer output when only one of the reference and sample arms is alternately blocked under a voltage is applied as in the case of acquisition process of the above frequency spectrum of the interference output with a sample voltage-on, which corresponds to the measured spectrum of the other arm not blocked, and then by excluding this spectrum from the frequency spectrum of the sample voltage-on case, i.e., from the one obtained in the above process; (vi) a process calculating phase difference values for the sample voltage-on case from the above normalized interference fringe spectrum of the sample voltage-on case as a function of a frequency change from the predetermined particular reference frequency; (vii) determining data-fitting functions for each set of the reference phase difference values of the sample voltage-off case and the phase difference values of the sample voltage-on case; and (viii) a process calculating an electro-optic coefficient value from a reference phase difference value ($\phi(f_0)$) of the sample voltage-off case and a phase difference value ($\psi(f_0)$) of the sample voltage-on case at a frequency ($f_o$) calculated by using the determined fitting functions after calculation of their difference ($\phi(f_0)-\psi(f_0)$) with a refractive index value calculated from a Sellmeier equation or a measured refractive index value at the frequency.

In order to achieve another goal of the present invention, a method of measuring a thermo-optic coefficient is provided by (A) using a light source for outputting an optical beam of multi-wavelengths, an optical interferometer for dividing the optical beam received from the light source into two separate beams, (B) supplying each of the two optical beams to a reference arm and a sample arm, respectively, having an optical sample to be measured on the sample arm, (C) combining the two beams, each passed through one of the reference and sample arms respectively, together to produce an interfered optical beam output, and an optical spectrum analyzing device for receiving the interfered optical beam output from the optical interferometer and analyzing its spectrum characteristics, and (D) including procedures composed of: (a) a process obtaining a reference frequency spectrum, directly or converting the wavelength into the frequency after measuring a wavelength spectrum, from the interferometer output while no heat is applied to the optical sample; (b) another process obtaining a normalized reference interference fringe spectrum by measuring a spectrum of the interferometer output when only one of the reference and sample arms is alternately blocked under no heat is applied as in the case of the above reference frequency spectrum acquisition process, which corresponds to the measured spectrum of the other arm not blocked, and then by excluding this spectrum from the reference frequency spectrum obtained in the above process; (c) a process calculating reference phase difference values from the above normalized reference interference fringe spectrum as a function of frequency change from a predetermined particular reference frequency; (d) a process obtaining another frequency spectrum of the interference output with a sample heat-on, either directly or by converting the wavelength to its corresponding frequency after measuring a wavelength spectrum, from the optical interferometer when some heat is applied to the optical sample; (e) another process obtaining a normalized interference fringe spectrum of the interferometer with a sample heat-on, by measuring a spectrum of the interferometer output when only one of the reference and sample arms is alternately blocked under some heat is applied as in the case of acquisition process of the above frequency spectrum of the interference output with a sample heat-on, which corresponds to the measured spectrum of the other arm not blocked, and then by excluding this spectrum from the frequency spectrum of the sample heat-on case, i.e., from the one obtained in the above process; (f) a process calculating phase difference values for the sample heat-on case from the above normalized interference fringe spectrum of the sample heat-on case as a function of a frequency change from the predetermined particular reference frequency; (g) determining data-fitting functions for each set of the reference phase difference values of the sample heat-off case and the phase difference values of the sample heat-on case; and (h) a process calculating a thermo-optic coefficient value from a reference phase difference value ($\phi(f_0)$) the sample heat-off case and a phase difference value ($\psi(f_0)$) of the sample heat-on case at a frequency ($f_o$) calculated by using the determined fitting functions after calculation of their difference ($\phi(f_0)-\psi(f_0)$) with a refractive index value calculated from a Sellmeier equation or a measured refractive index value at the frequency and with a pre-known or measured thermal expansion coefficient.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
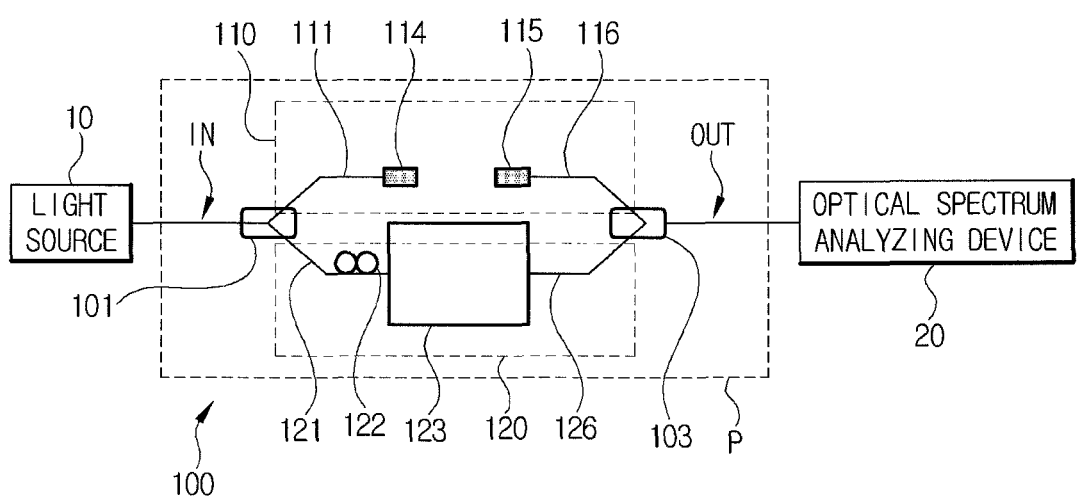
FIGS. 1A and 1B are diagrams each illustrating a system for measuring an electro-optic coefficient and a thermo-optic coefficient, according to embodiments of the present invention.

Hereinafter, the present invention will be described more fully with reference to the accompanying drawings, in which exemplary embodiments of the invention are shown. Meanings of terms or vocabularies used herein should not be limited to common or dictionary definitions, and are understood according to a technical aspect of the present invention based on the principle that an inventor can suitably define a concept of a term to describe the invention in the best way possible.

The invention may, however, be embodied in many different forms and should not be construed as being limited to the embodiments set forth herein; rather, these embodiments are provided so that this disclosure will be thorough and complete, and will fully convey the concept of the invention to those skilled in the art.

Systems for measuring electro-optic and thermo-optic coefficients by using interference fringe measurement, and methods of measuring electro-optic and thermo-optic coefficients by using the systems will now be described in detail with reference to accompanying drawings.

First, systems for measuring an electro-optic coefficient and a thermo-optic coefficient, according to embodiments of the present invention, will be described with reference to FIGS. 1A and 1B. In the drawings, like reference numerals denote like elements.

Figure 1B:
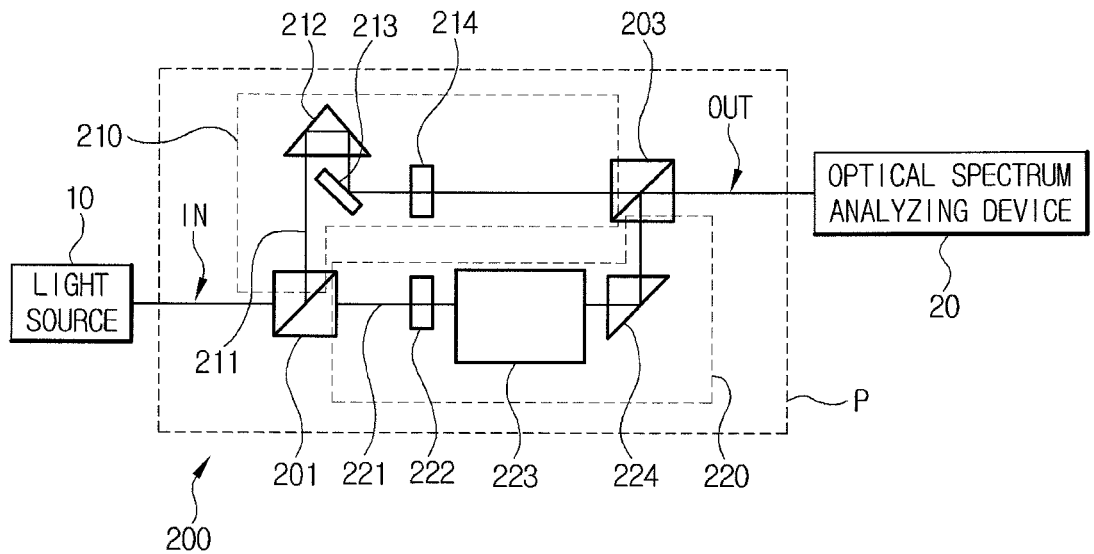

FIGS. 1A and 1B are diagrams each illustrating a system for measuring an electro-optic coefficient and a thermo-optic coefficient, according to embodiments of the present invention, wherein the system of FIG. 1A uses an optical fiber device, and the system of FIG. 1B includes a bulk type optical device, such as a prism.

The systems according to the embodiments of the present invention uses a Mach-Zehnder interferometer, and as shown in FIGS. 1A and 1B, the system includes a light source 10, an optical interferometer 100 or 200, and an optical spectrum analyzing device 20.

Here, the light source 10 outputs an optical beam of multi-wavelengths. Unlike the conventional technology that uses a single wavelength, the system measures optical characteristics in a wide wavelength region, and thus the light source 10 may support an output of multi-wavelengths.

First, the optical interferometer 100 included in the system of FIG. 1A may consist of an optical beam splitter, which divides the optical beam received from the light source 10 through an input optical path IN into two beams, each for one of the arms, i.e., a reference arm 110 and the other sample arm 120 connected to a sample installation stand 123 containing an optical sample, and an optical beam combiner, which combines the two beams, each passed through one of the reference arm 110 and the sample arm 120 respectively, together to produce an interfered optical beam output.

Here, an optical fiber type beam splitter 101 is used as the optical beam dividing means, and an optical fiber type beam combiner 103 is used as the optical beam combining means.

Meanwhile, the optical spectrum analyzing device 20 receives the interfered optical beam from the optical interferometer 100 through its output optical path OUT, and analyses their spectral information.

Here, the reference arm 110 includes a reference arm optical path 111 that has a separated free space region in the middle, and the sample arm 120 includes a sample arm optical path 121.

According to the system of FIG. 1A, a pair of optical collimators 114 and 115 are respectively connected to the two free-space separated ends of the reference arm optical path, thereby transmitting an optical beam into the air. Here, the reference arm 110 may have an adjustable air path length for the optical beam transmission by adjusting the interval between the two optical collimators 114 and 115.

Here, at least one of the reference arm optical path 111 near the beam splitter 101 and the reference arm optical path 116 near the optical beam combiner 103 may be an optical fiber path so that the reference arm optical path 111 is movable for the optical beam path adjustment.

Meanwhile, an interval between the optical collimators 114 and 115 may be adjusted while they are supported by a predetermined external structure for stabilization of a measuring environment, and if required, GRIN lenses may be used instead of the two optical collimators.

A polarization controller 122 and a sample installation stand 123 with either electrical or thermal control of the sample environment are placed in the middle of the sample arm optical path 121, i.e., an optical path between the optical fiber type optical beam splitter 101 and an optical sample S. The optical beam passing through the polarization controller 122 and the sample installation stand 123 meet with the beam that passed through the reference arm 110, at the optical fiber type optical beam combiner 103.

Here, the sample arm optical path 121 near the optical beam splitter 101 and/or the sample arm optical path 126 near the optical beam combiner 103 may also be an optical fiber path so as to have an easy adjustment of its length.

Moreover, the input optical path IN from the optical source 10, the optical beam splitter 101, the optical beam combiner 103, and the output optical path OUT may be composed of optical fiber-type components and paths, as shown in FIG. 1A.

In addition, a vibration isolation shield P may be formed by surrounding the entire optical interferometer 100 so as to block any effect caused by external vibrations in an accurate data measurement procedure.

Unlike using optical fiber-type devices and optical fiber paths as illustrated in FIG. 1A, the system of FIG. 1B uses bulk optics, and thus uses a bulk-optics-type beam splitter 201 instead of the optical fiber-type beam splitter 101 as a means of the optical beam divider, and a bulk-optics-type beam combiner 203 instead of the optical fiber-type beam combiner 103 as a means of the optical beam combiner.

Also, a first beam refractive means including a retro-reflector 212 and a mirror 213 is used so that a length of an optical path may be adjusted while the optical beam from the light source 10 passes through the reference arm 210.

A rectangular angle reflection prism 224, as a second beam refractive means, formed of the same material as the retro-reflector 212 is used so that the optical beam passing through the sample arm 220 combines with the optical beam that passed through the reference arm 210, in the beam combiner 203, thereby forming an interference fringe.

Half-wave-plate-type polarization controllers 214 and 222 may be included for each of the reference and sample arms 210 and 220 so that polarizations of the optical beam passing through the reference arm 210 and the optical beam passing through the sample arm 220 are aligned to each other's at the beam combiner 203 and proceed to the output optical path OUT.

According to the current embodiment of the present invention, a length of an optical beam path in the reference arm 210 may be adjusted by moving the position of the retro-reflector 212 back and forth.

Figure 2A:
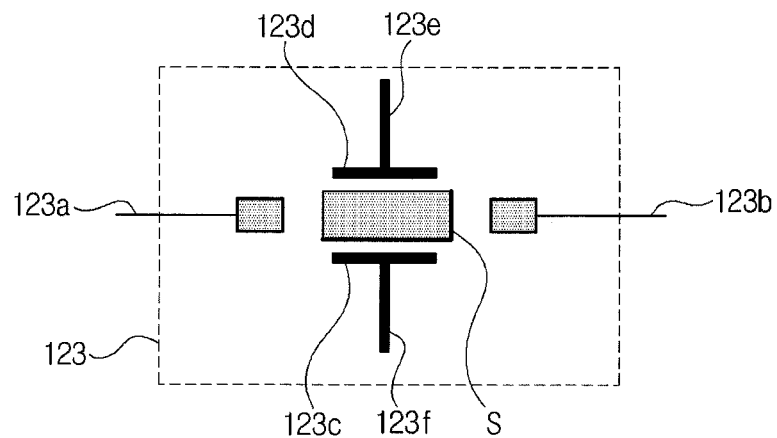
FIGS. 2A through 2C are diagrams each illustrating main elements of a sample installation stand of FIG. 1A, for a sample arm to measure an electro-optic coefficient.

Referring back to FIG. 1A, in order to measure an electro-optic coefficient of the optical sample S, electrodes 123c and 123d for applying a voltage to the optical sample S, and electrode terminal wires 123e and 123f for supplying electricity to the electrodes 123c and 123d may be included inside the sample installation stand 123 for installing the optical sample S, as shown in FIG. 2A.

Here, the electrodes 123c and 123d may contact the optical sample S in locations that do not overlap with the optical beam passing through the optical sample S so as to apply the voltage to the optical sample S.

For example, as shown in FIG. 2A, the electrodes 123c and 123d may contact the locations perpendicular to a surface on which the optical beam is irradiated, so that the optical beam is easily transmitted.

When optical fibers are used in optical paths as in FIG. 1A, the optical sample S is placed between a pair of optical connection means 123a and 123b. The optical connection means 123a and 123b may be either optical collimators or GRIN lenses if the optical sample S is a general bulk type, or may be composed of tapered optical fiber ends if the optical sample S is an optical waveguide-type device.

When a bulk-type optical path is used as in FIG. 1B, a beam is directly irradiated, and thus the optical connection means 123a and 123b are not used.

Figure 2B:
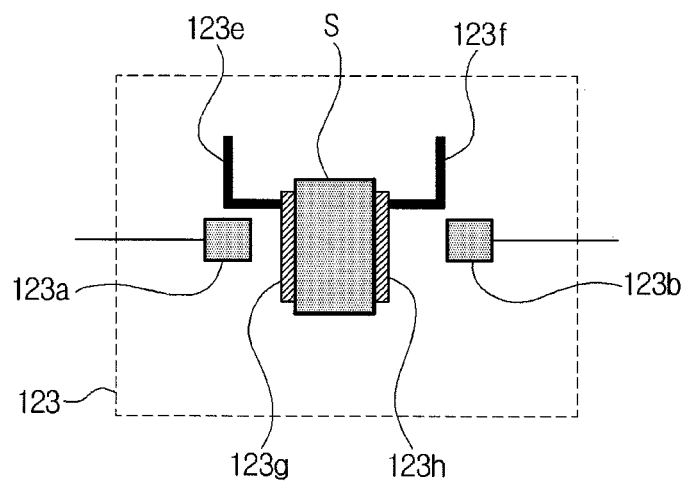

The sample installation stand 123 may have a different structure from that of FIG. 2A. As shown in FIG. 2B, transparent electrodes 123g and 123h for applying a voltage to the optical sample S by contacting the optical sample S at locations that overlap with the optical beam passing through the optical sample S are used. Here, since the optical beam can pass through the transparent electrodes 123g and 123h, locations of the transparent electrodes 123g and 123h are not limited.

Figure 2C:
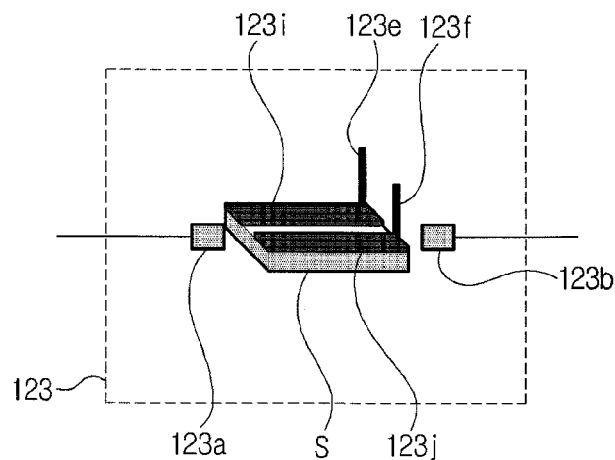

The structure of the sample installation stand 123 may be different from above, and as shown in FIG. 2C, two electrodes 123i and 123j are formed on one surface of the thin optical waveguide type sample S at a uniform interval, an optical beam may be transmitted near the electrodes 123i and 123j along the interval between the electrodes 123i and 123j, and a voltage is applied to the sample S through the electrodes 123i and 123j.

In this case, electro-optic characteristics may be directly measured in an optical waveguide type structure made of an optical waveguide-type electro-optic material.

Figure 2D:
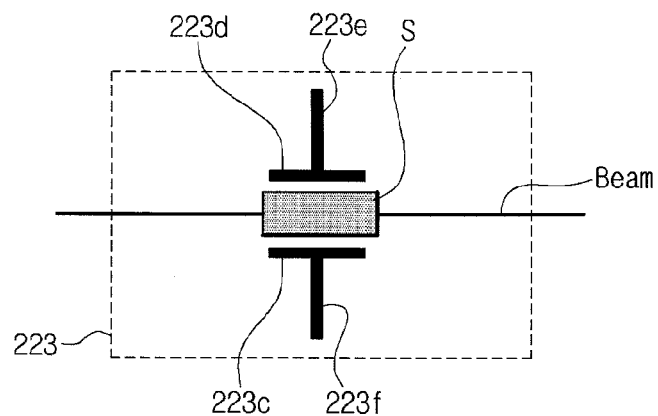
FIGS. 2D through 2F are diagrams each illustrating main elements of a sample installation stand of FIG. 1B, for a sample arm to measure an electro-optic coefficient.
Figure 2E:
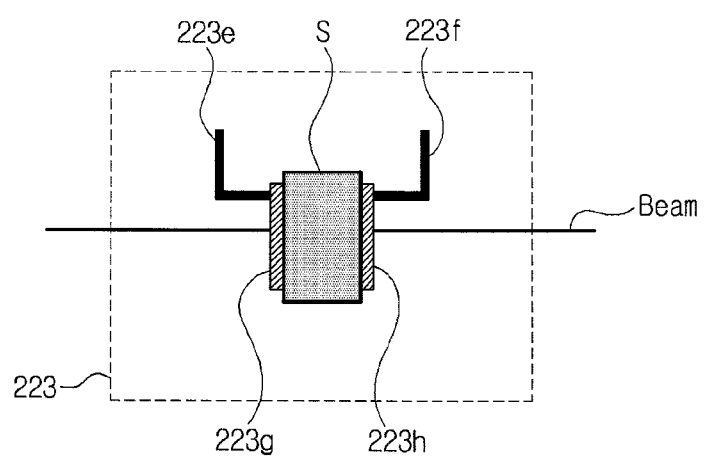
Figure 2F:
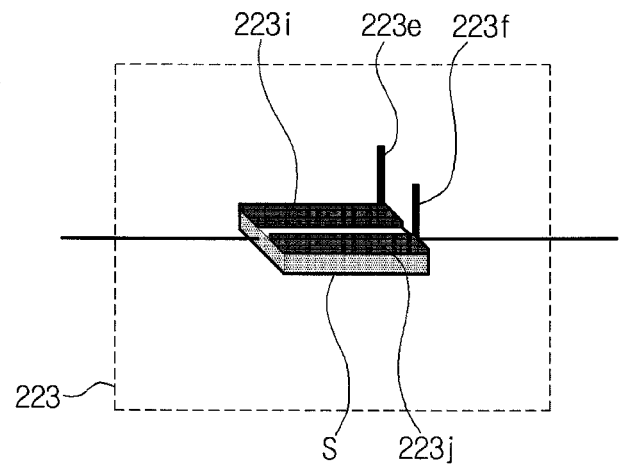

FIGS. 2D through 2F are diagrams for describing a direction of light transmitted to the sample S prepared respectively as in FIGS. 2A through 2C being adjusted, when an electro-optic coefficient is measured by using the bulk-optic system of FIG. 1B.

Here, the principles are the same except that the optical connection means 123a and 123b are not used, and thus overlapping descriptions thereof will not be repeated.

Figure 3A:
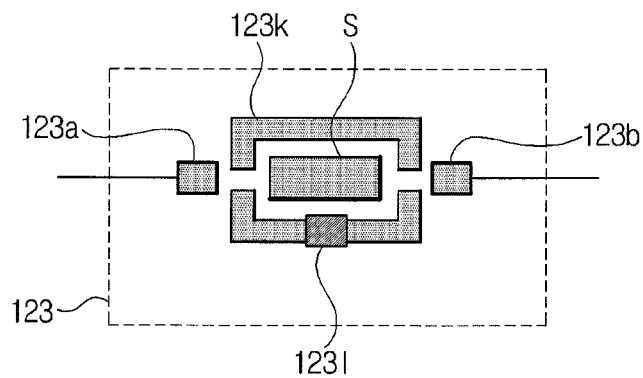
FIGS. 3A and 3B are diagrams respectively illustrating the main elements of the sample installation stands of FIGS. 1A and 1B, for the sample arm to measure a thermo-optic coefficient.
Figure 3B:
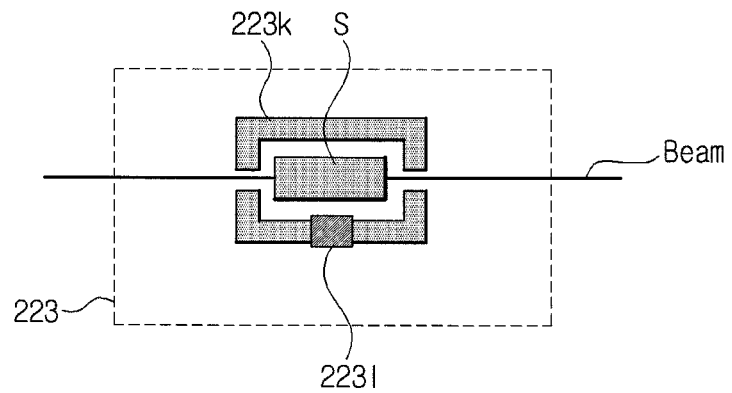

Meanwhile, in order to measure a thermo-optic coefficient of the sample S, heating and cooling apparatuses 123k and 223k for increasing or decreasing a temperature of the optical sample S, and temperature sensors 123l and 223l for measuring the temperature of the optical sample S may be included around the optical sample S, as shown in FIGS. 3A and 3B.

The heating and cooling apparatuses 123k and 223k increase or decrease the temperature of the optical sample S so that interference fringes at various temperatures are measured. As shown in FIGS. 3A and 3B, the heating and cooling apparatuses 123k and 223k may not block a path of the optical beam transmitting through the optical sample S.

Here, the heating and cooling apparatuses 123k and 223k may be controlled by a central control unit (not shown) for managing the overall experiments, based on the temperature of the optical sample S measured by the temperature sensors 123l and 223l.

Systems for measuring each of the electro-optic and thermo-optic coefficients, according to other embodiments of the present invention, will now be described with reference to FIGS. 4A and 4B. Here, reference numerals of FIGS. 4A and 4B that are identical to those of FIGS. 1A through 3B denote the same functional elements.

Figure 4A:
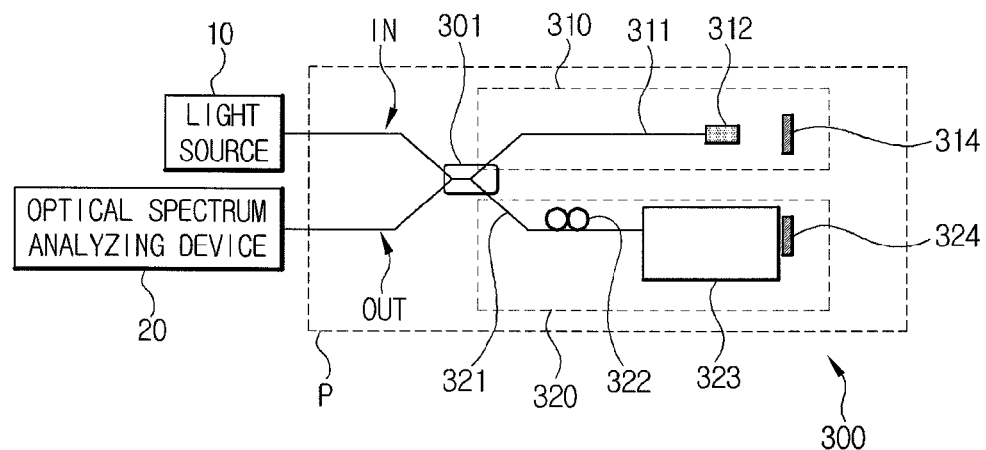
FIGS. 4A and 4B are diagrams each illustrating another system for measuring an electro-optic coefficient and a thermo-optic coefficient, according to embodiments of the present invention.
Figure 4B:
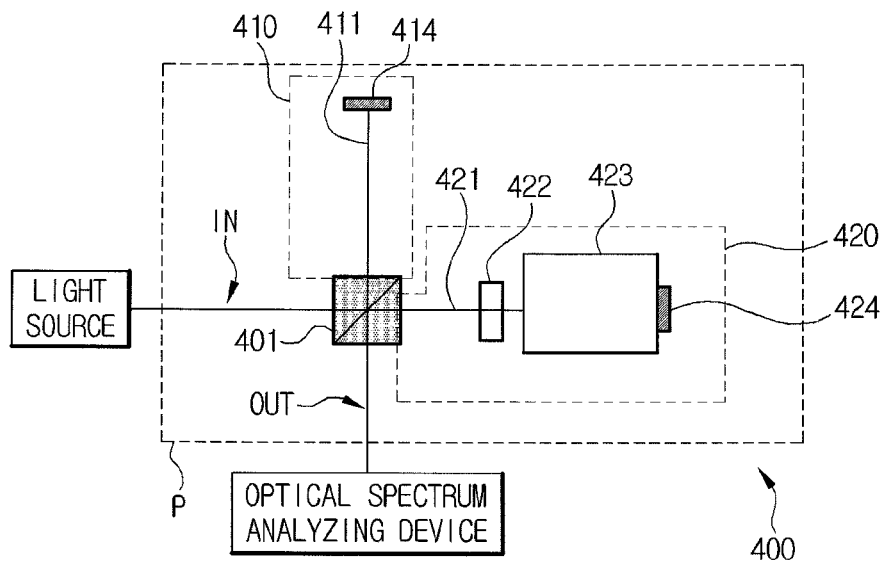
Figure 5A:
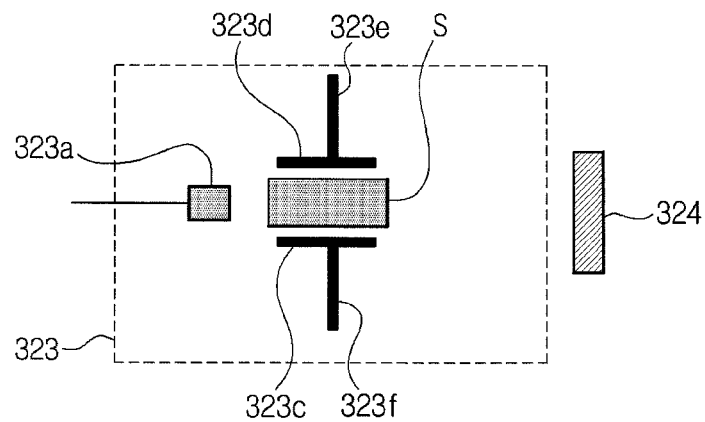
FIGS. 5A through 5C are diagrams each illustrating main elements of a sample installation stand of FIG. 3A, for a sample arm to measure an electro-optic coefficient.
Figure 5B:
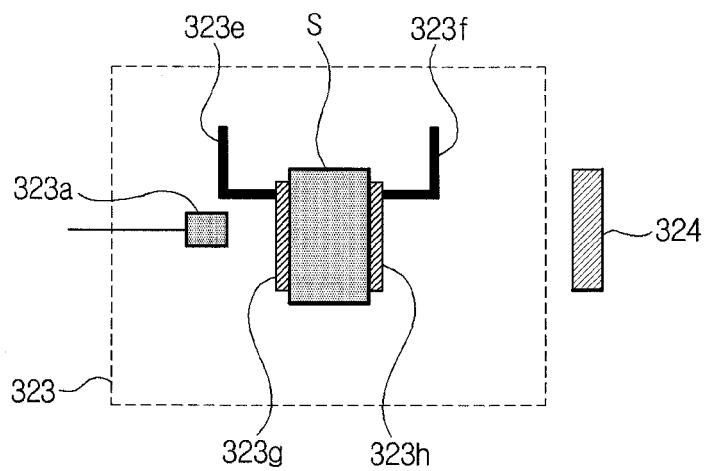
Figure 5C:
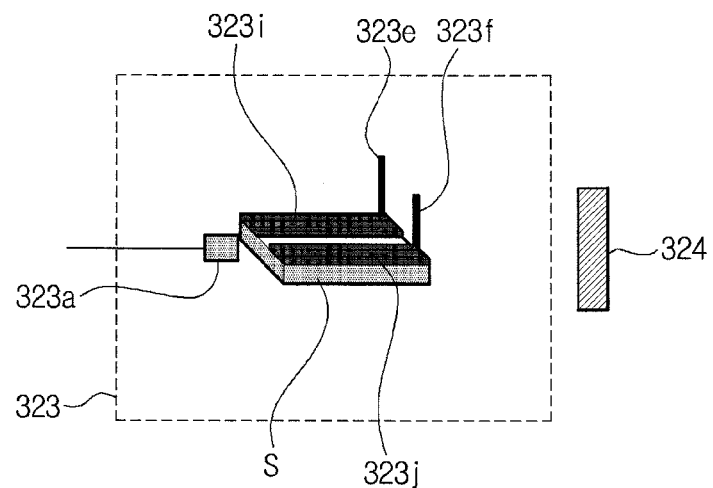
Figure 5D:
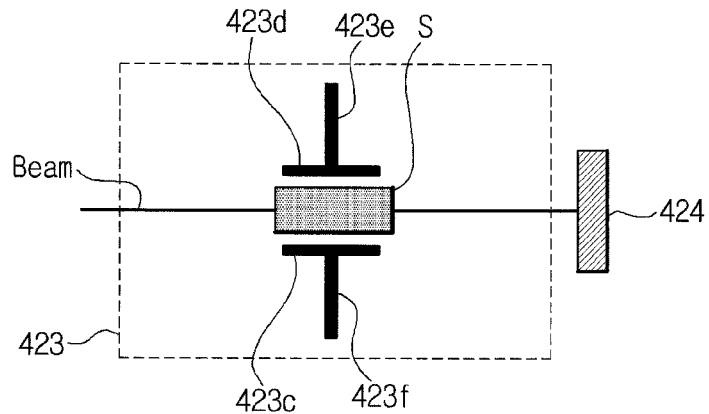
FIGS. 5D through 5F are diagrams each illustrating main elements of a sample installation stand of FIG. 3B, for a sample arm to measure an electro-optic coefficient.
Figure 5E:
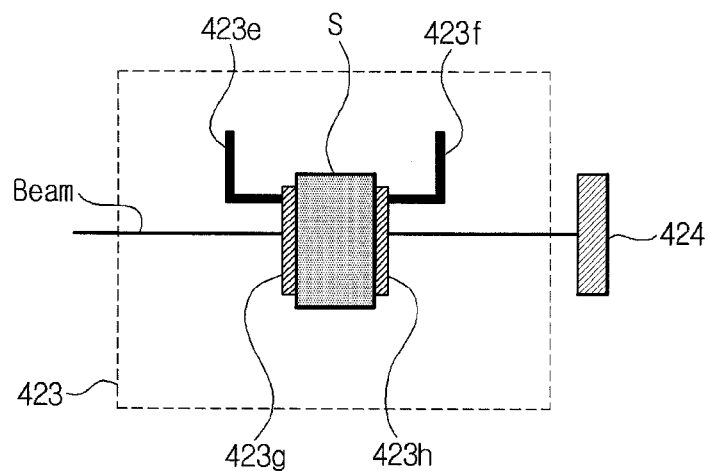
Figure 5F:
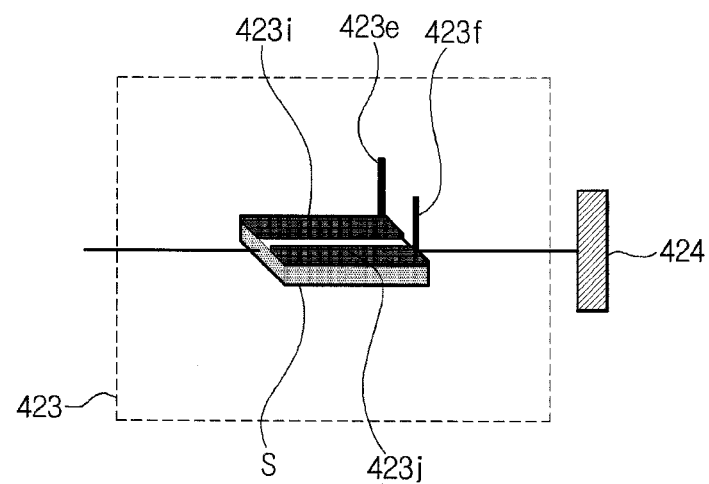

The systems of FIGS. 4A and 4B use a Michelson interferometer. An optical interferometer 300 or 400 includes an optical beam dividing and combining unit (301 or 401), which divides an optical beam received from the light source 10 into two beams and combines the two optical beams returning from the divided directions to produce an interference beam output, a reference arm 310 or 410, which reflects and returns one of the optical beams to the optical beam dividing and combining unit, and a sample arm 320 or 420 for penetrating the other optical beam through the optical sample S to be measured and then reflecting and returning the other optical beam to the optical beam dividing and combining unit, and for applying a voltage or some heat to the optical sample S.

Most of the operating principles of the systems of FIGS. 4A and 4B are similar to those of the systems of FIGS. 1A and 1B, except one different aspect about that the optical beams exited from the reference arm 310 or 410 and the sample arm 320 or 420 return back to their output ports of the arms.

Accordingly, the system of FIG. 4A using optical fiber based optical paths includes an optical fiber coupler 301 as the optical beam dividing and combining unit, and each of the reference arm 310 and the sample arm 320 include one of the reflectors 314 and 324, respectively.

Thus, the optical beams passed through the reference arm 310 and the sample arm 320 through the optical fiber coupler 301, are reflected back to the optical fiber coupler 301, are interfered with each other, and then are inputted into the optical spectrum analyzing device 20.

In FIG. 4A, the reference arm 310 may include an optical beam transmitting and receiving unit 312, which outputs the optical beam received from the optical fiber coupler 301 into the air and receives the optical beam reflected from the reflector 314. The optical beam transmitting and receiving unit 312 may be an optical collimator or GRIN lens.

An optical path 311 between the optical fiber coupler 301 and the optical beam transmitting and receiving unit 312 may be an optical fiber path so that a length of the optical path 311 is easily adjustable.

Similarly, the sample arm 320 includes the reflector 324 for reflecting the optical beam received through a sample installation stand 323 back toward the optical fiber coupler 301. A polarization controller 322 for adjusting a polarization direction of the optical beam irradiated to the optical sample S may be disposed on an optical path 321 between the optical fiber coupler 301 and the optical sample S.

Meanwhile, the system of FIG. 4B using bulk-type optical paths contains an optical beam splitter 401, which branches the optical beam irradiated from the light source 10 into two directions, i.e. parallel and perpendicular directions to an irradiation direction, as the optical beam dividing and combining unit.

Here, the reference arm 410 includes a reflector 414 for transmitting one of the optical beams branched by the optical beam splitter 401 back to the optical beam splitter 401.

In this case, the optical beam transmission length can be adjusted by moving the position of the reflector 414 back and forth.

Also, the sample arm 420 includes a reflector 424 for transmitting the other optical beam branched by the optical beam splitter 401 back to the optical beam splitter 401 through a sample installation stand 423. A half-wave plate type polarization controller 422 for adjusting a polarization direction of an optical beam may be disposed on an optical path 421 between the optical beam splitter 401 and the optical sample S so that polarizations of the two separated optical beams are matched in the optical beam splitter 401 before proceeding to the output optical path OUT.

FIGS. 5A through 5F illustrate detailed structures for measuring an electro-optic coefficient of a sample in the systems of FIGS. 4A and 4B.

As shown in FIGS. 5A through 5F, the basic structures for applying a voltage in the systems of FIGS. 4A and 4B are identical to those in FIGS. 1A and 1B, and thus detailed descriptions thereof are not repeated.

However, since the systems of FIGS. 4A and 4B have a function of reflecting and transmitting back the optical beams, an optical connection means 323a, which irradiates the optical beam over the optical sample S and receives the optical beam that is reflected back from the reflector 324 via the optical sample S, is included only on an opposite side of the reflector 324, in the system of FIG. 4A that uses a fiber-type optical path.

Also here, the optical path 321 between the optical coupler 301 and the optical connection means 323a may be an optical fiber path.

Figure 6A:
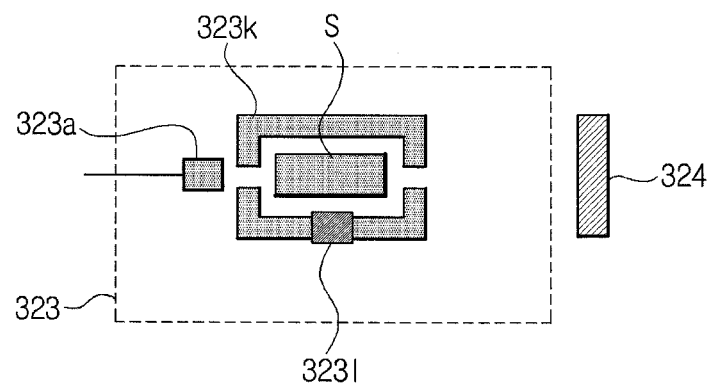
FIGS. 6A and 6B are diagrams respectively illustrating the main elements of the sample installation stands of FIGS. 3A and 3B, for the sample arm to measure a thermo-optic coefficient.
Figure 6B:
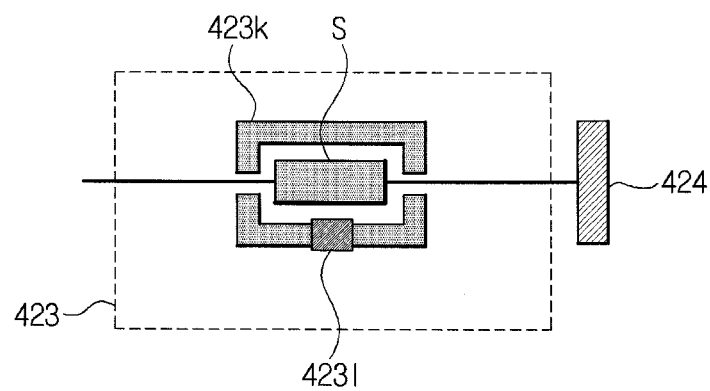

However, in the system of FIG. 4B using bulk-type optical paths, the optical connection means 323a is not required Meanwhile, in order for the system of FIGS. 4A and 4B to measure a thermo-optic coefficient of the optical sample S, the systems of FIGS. 4A and 4B may respectively include heating and cooling apparatuses 323k and 423k, which increase or decrease the temperature of the optical sample S, and temperature sensors 323l and 423l, which measures the temperature of the optical sample S, around the optical sample S as illustrated in FIGS. 6A and 6B.

A method of measuring an electro-optic coefficient and a thermo-optic coefficient by using the system described above will now be described with reference FIG. 7. Reference notations of FIG. 7 that are identical to those of FIGS. 1 through 6 denote the same elements. Also, the reference notations used below are based on FIG. 1A, but only representative elements are denoted for understanding of the present invention, and thus are not limited thereto.

Figure 7:
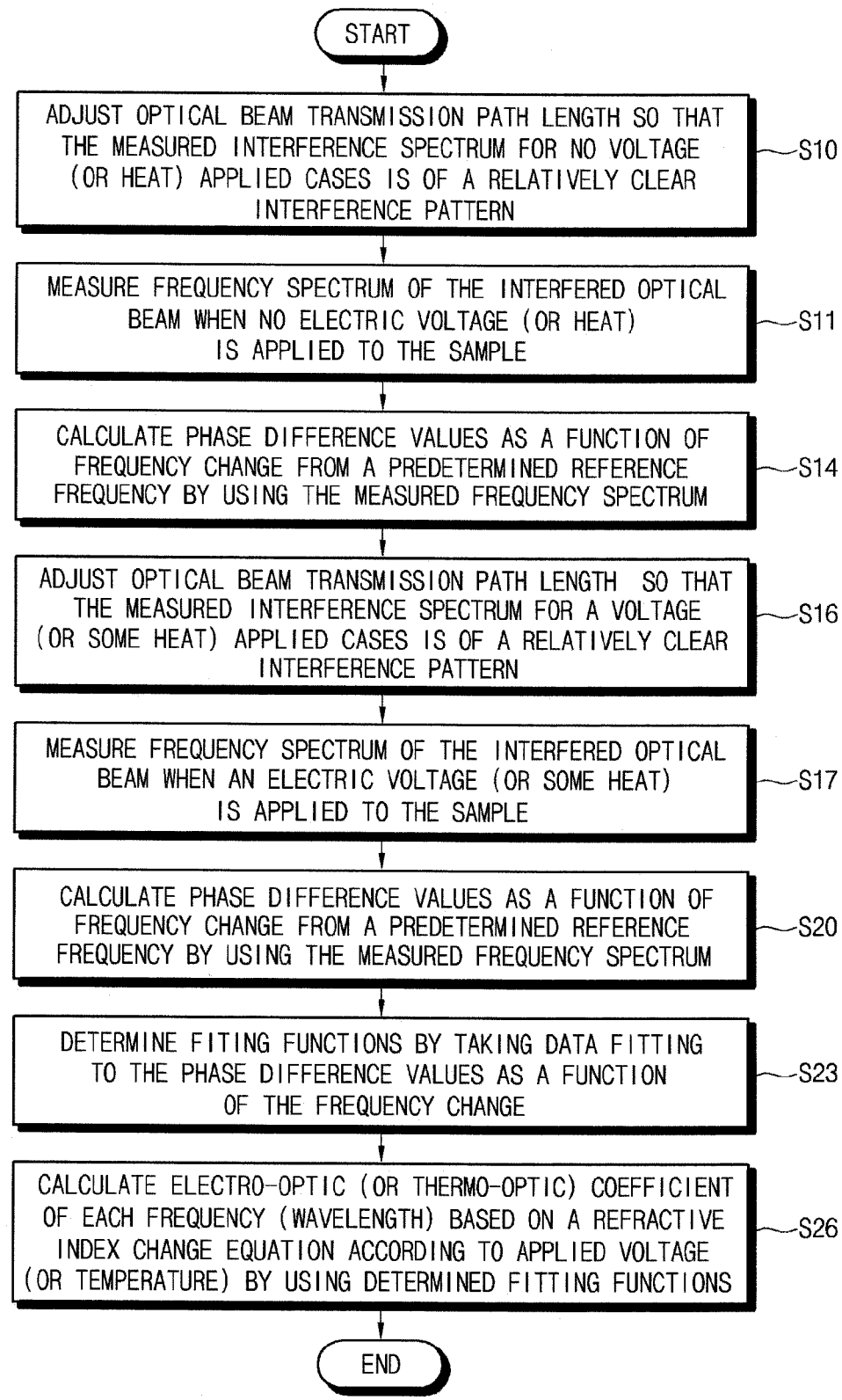
FIG. 7 is a flowchart illustrating a method of measuring an electro-optic coefficient or a thermo-optic coefficient, according to an embodiment of the present invention.

FIG. 7 is a flowchart illustrating a method of measuring an electro-optic coefficient or a thermo-optic coefficient, according to an embodiment of the present invention.

According to the current embodiment of the present invention, a frequency spectrum is obtained by measuring a spectrum of an optical output beam of the optical interferometer with the optical spectrum analyzing device 20 when no heat or voltage is applied to the optical sample S of the sample arm 120, and by converting the wavelength to the frequency, in operation S11.

Here, the operation S11 may be performed by measuring a spectrum output through the optical interferometer 100 while no voltage (or heat) is applied to the optical sample S and converting the wavelength to the frequency to obtain a frequency spectrum (reference spectrum), by measuring the interferometer output spectrum while the light transmission through one of two arms (reference arm 110 and sample arm 120) of the optical interferometer 100 is blocked at the same voltage (or heat) condition as for the reference spectrum case, which corresponds to a spectrum of the unblocked arm, and then excluding the spectrum of the unblocked arm from the reference spectrum to obtain a pure interference fringe spectrum.

Alternatively, the operation S11 may be performed by measuring a spectrum output through the optical interferometer 100 while no voltage (or heat) is applied to the optical sample S and converting the wavelength to the frequency to obtain a frequency spectrum (reference spectrum), and then by excluding the spectral intensity distribution values of the optical beam calculated with a Hilbert transform from the reference spectrum to obtain a pure interference fringe spectrum.

Here, the spectral intensity distribution values of the optical beam calculated with a Hilbert transform are obtained by using a well-known computational or mathematical method.

An optical beam transmission length of the reference arm 110 in the air may be adjusted first in operation S10 so that the spectrum measured by the optical spectrum analyzing device 20 shows a relatively clear interference pattern. Here, the state representing a relatively clear interference pattern corresponds to a state of the maximum visibility of the interference fringe, i.e., a state when the interference fringe is seen most clearly.

Then, in operation S14 the phase difference values as a function of the frequency change from a predetermined reference frequency are calculated from the frequency spectrum obtained in operation S11.

Since the phase difference between two adjacent peak points of the frequency spectrum obtained in operation S11 is $2\pi$, the phase difference values as a function of the frequency change may be calculated from the predetermined reference frequency by using such peak points.

Generally, the peak points denote upward peak points, but the peak points used in operation S14 may be downward valley points.

Next, the optical spectrum analyzing device 20 measures a spectrum of the optical beam outputted through the optical interferometer 100 while a voltage (or some heat) is applied to the optical sample S of the sample arm 120, in operation S17.

Similarly in operation S11, operation S17 may be performed by measuring a spectrum output through the optical interferometer 100 while a voltage (or some heat) is applied to the optical sample S and converting the wavelength to the frequency to obtain a frequency spectrum (i.e., a voltage-on frequency spectrum), by measuring the interferometer output spectrum while the light transmission through one of two arms (reference arm 110 and sample arm 120) of the optical interferometer 100 is blocked at the same voltage (or heat) condition as for the voltage-on frequency spectrum case, which corresponds to a spectrum of the unblocked arm, and then excluding the spectrum of the unblocked arm from the voltage-on frequency spectrum to obtain a pure interference fringe spectrum Alternatively, operation S17 may be performed by measuring a spectrum output through the optical interferometer 100 while a voltage (or some heat) is applied to the optical sample S and converting the wavelength to the frequency to obtain a frequency spectrum (i.e., a voltage-on frequency spectrum), and then by excluding the spectral intensity distribution values of the optical beam calculated with a Hilbert transform from the voltage-on frequency spectrum to obtain a pure interference fringe spectrum.

Here, before operation S17, an optical beam transmission length of the reference arm 110 in the air may be adjusted in operation S16 to achieve a relatively clear interference pattern.

Next, the phase difference values as a function of the frequency change is calculated in operation S20 from the predetermined reference frequency by using the frequency spectrum obtained in operation S17.

Here, since the phase difference between two adjacent peak points of the frequency spectrum obtained in operation S17 is identical to that of the frequency spectrum obtained in operation S11, the phase difference values may be calculated from the predetermined reference frequency in operation S20 as it is done in operation S14.

Here, the peak points in operation S20 may be upward peak points or downward valley points as in operation S14.

Next, in operation S23 data fitting functions and their coefficients are determined for curves of the phase difference values calculated in operations S14 and S20.

Last, an electro-optic coefficient value (or a thermo-optic coefficient value) is calculated in operation S26 by using the coefficients of the data fitting functions determined in operation S23.

While calculating a thermo-optic coefficient, a pre-known or pre-measured thermal expansion coefficient value is used.

The method of measuring an electro-optic coefficient and a thermo-optic coefficient by using the system of measuring electro-optic and thermo-optic coefficients with interference fringe measurement, according to an embodiment of the present invention, will now be described in detail with reference to equations for obtaining an electro-optic coefficient (or thermo-optic coefficient) of an optical sample.

First, magnitudes of the electric fields of optical beams transmitting through the reference arm 110 and the sample arm 120 of the optical interferometer 100 for both cases with an electric field or some heat applied to the optical sample S and without any electric field or heat applied to the optical sample S can be expresses, as functions of the frequency, as in Equations 1 and 2 below.

$$E_A = E_0 \exp[-j\beta_A L_A] \cdot \exp[-j2\pi f t_0] \cdot \exp[j2\pi f t] \qquad \text{[Equation 1]}$$

$$E_B = aE_0 \exp[-j\beta_S L_S] \cdot \exp[-j\beta_B L_B] \cdot \exp[j2\pi f t] \qquad \text{[Equation 2]}$$

Here, $E_o$ denotes an amplitude of an optical beam proceeding to the reference arm 110 after being divided by the optical fiber-type beam splitter 101, and a denotes a relative ratio of an electric field amplitude of an optical beam proceeding to the sample arm 120 to the electric field amplitude of the optical beam proceeding to the reference arm 110.

Also, $L_A$ corresponds to a length of an optical waveguide when a part of the reference arm optical path 111 of the optical interferometer 100 is an optical waveguide, and $t_o$ is zero when the optical interferometer 100 is composed of free-space bulk optics. $L_B$ denotes an entire length of the sample arm's optical path 121 of the optical interferometer 100 excluding the length of the optical sample S, and $L_S$ denotes the length of the optical sample S.

$\beta_A$ and $\beta_B$ respectively denote wave propagation constants of the optical beams proceeding to the reference arm's optical path 111 and the sample arm's optical path 121, respectively. $\beta_S$ denotes a wave propagation constant of the optical beam penetrating the optical sample S, wherein $$\beta_s = nk_0 = \frac{2\pi n}{\lambda_0} = \frac{2\pi f}{c} n.$$

Here, c denotes a speed of light in the air, and n denotes an effective refractive index of the optical sample S.

When an optical waveguide is used in the sample arm's optical path 121, and there is an air space between the optical waveguide and the optical sample S, then $L_B = L_{B,wg} + L_{air}$ for the entire length of the sample arm's optical path 121, and $\beta_B = \beta_{B,wg} + \beta_{air}$.

Meanwhile, $t_o$ may be d/c, i.e. a time taken for the light to pass through a air interval length d between the optical collimators 114 and 115 of the reference arm 110.

Intensity of the optical beam output from the output optical path OUT of the optical interferometer 100 may be calculated according to Equation 3 below.

$$I(f)=|E_A+E_B|^2=|E_0|^2\{1+\alpha^2\}+2a|E_0|^2\cos\phi(f)=I_A+I_B+2\sqrt{I_AI_B}\cos\phi(f) \quad \text{[Equation 3]}$$

Here, $I_A$ and $I_B$ respectively denote intensities of the optical beams passing through the reference arm 110 and the sample arm 120 of the optical interferometer 100, wherein $I_A=|E_A|^2$ and $I_B=|E_B|^2$.

Also, the phase difference between two beams propagating through the reference arm 110 and the sample arm 120 may be calculated according to Equation 4 below.

$$\phi(f) = \{\beta_A L_A - \beta_B L_B\} + 2\pi f t_0 - \beta_S L_S \quad \text{[Equation 4]}$$
$$= 2\pi f\left[\tau_{AB}(f) + t_0 - \frac{n(f)L_S}{c}\right]$$

Meanwhile, if Equation 4 is expressed in terms of a time delay $\tau_{AB}(f)$ between the optical beams passing through the reference arm 110 and the sample arm 120, Equation 5 is defined.

$$B_A L_A - B_B L_B = 2\pi f \tau_{AB}(f) \quad \text{[Equation 5]}$$

Next, as shown in FIG. 2A, when an external voltage V is applied to the optical sample S connected between the optical connectors 123a and 123b, the magnitude of the electric field as a function of frequency of the optical beam passing through the sample arm 120 of the optical interferometer 100 is calculated as Equation 6 below.

$$E'_B(f)=aE_0\exp[-j\beta'_S L'_S]\cdot\exp[-j\beta_B L_B]\cdot\exp[j2\pi ft] \quad \text{[Equation 6]}$$

Here, $\beta'_S$ denotes a wave propagation constant of the optical beam transmitted into the optical sample S, when the voltage V is applied between the electrodes 123c and 123d of the optical sample S, or when the temperature of the optical sample S is raised or lowered by the heating and cooling apparatus 123k.

As well known, for an electro-optic coefficient measurement, the wave propagation constant may be calculated according to $$\beta'_S = n'k_0 = \frac{2\pi n'}{\lambda_0} = \frac{2\pi f}{c}\left[n(f) - \frac{1}{2}n^3(f)r\frac{V}{w}\right] = \beta_S - \frac{\pi f}{c}n^3(f)r\frac{V}{w},$$

and for a thermo-optic coefficient measurement, the wave propagation constant may be calculated according to $$\beta'_S = n'k_0 = \frac{2\pi n'}{\lambda_0} = \frac{2\pi f}{c}\left[n(f, T_0) + \frac{dn}{dT}\Delta T\right] = \beta_S + \frac{2\pi f}{c}\frac{dn}{dT}\Delta T.$$

Here, r denotes a linear electro-optic coefficient, and w denotes a thickness of the optical sample and identical to an interval between the electrodes 123c and 123d.

dn/dT denotes a thermo-optic coefficient of the optical sample S. $T_o$ denotes an initial temperature before it is being changed, and $\Delta T$ denotes a temperature change.

$L'_s$ denotes a final length changed by a piezoelectric effect after the voltage V is applied when an electro-optic coefficient is measured, and is generally identical to the original length $L_S$ if there is no large change.

However, when a thermo-optic coefficient is measured, $L'_s$ denotes a length of the optical sample after the temperature change $\Delta T$, and may be calculated according to $L'_S=L_S[1+\alpha\Delta T]$ by using a known thermal expansion coefficient $\alpha$, or by using an apparatus for measuring thermal expansion.

Intensity of the optical output beam emerging from the output optical path OUT through the optical interferometer 100 may be calculated according to Equation 7 below.

$$I_S(f)=|E_0|^2\{1+\alpha^2\}+2\alpha|E_0^2|\cos\{\psi(f)\} \quad \text{[Equation 7]}$$

Here, the phase difference between two beams propagating through the reference arm 110 and the sample arm 120 may be calculated according to Equation 8 below.

$$\psi(f)=\{\beta_A L_A-\beta_B L_B\}+2\pi ft_0-\beta'_S L'_S \quad \text{[Equation 8]}$$

When Equation 8 is substituted with Equation 4, the phase difference value may be calculated according to Equations 9 and 10, respectively, when an electro-optic coefficient is measured and when a thermo-optic coefficient is measured.

$$\psi(f) = \phi(f) + \frac{\pi f}{c}n^3(f)r\frac{V}{w}L_S \quad \text{[Equation 9]}$$

$$\psi(f) = \{3_A L_A - 3_B L_B\} + 2\pi ft_0 - 3'_S L'_S \quad \text{[Equation 10]}$$
$$= \{3_A L_A - 3_B L_B\} + 2\pi ft_0 -$$
$$\left[3_S + \frac{2\pi f}{c}\frac{dn}{dT}\Delta T\right][L_S(1+\alpha\Delta T)]$$
$$= \{3_A L_A - 3_B L_B\} + 2\pi ft_0 - 3_S L_S -$$
$$3_S L_S \alpha\Delta T - \frac{2\pi f}{c}\frac{dn}{dT}\Delta T L_S(1+\alpha\Delta T)$$
$$= \phi(f) - 3_S L_S \alpha\Delta T - \frac{2\pi f}{c}\frac{dn}{dT}\Delta T L_S(1+\alpha\Delta T)$$
$$= \phi(f) - \frac{2\pi f L_S(T_0)\Delta T}{c}\left[\begin{array}{l}n(f, T_0)\alpha + \\ \frac{dn}{dT}\{1+\alpha\Delta T\}\end{array}\right]$$

Here, $n(f,T_0)$ denotes a refractive index of the optical sample S in a frequency f at the initial temperature $T_0$, and $L_s(T_0)$ denotes an original length of the optical sample S at the initial temperature $T_0$.

An electro-optic coefficient may be summarized according to Equation 11 below, based on Equation 9.

$$r(f) = \frac{cw}{\pi f V L_S n^3(f)}[\psi(f) - \phi(f)] \quad \text{[Equation 11]}$$

Also, a thermo-optic coefficient may be summarized according to Equation 12 below, based on Equation 10.

$$\frac{dn(f)}{dT} = \frac{1}{\{1+\alpha\Delta T\}}\left[\frac{c}{2\pi f L_S(T_0)\Delta T}\left\{\begin{array}{l}\phi(f) - \\ \psi(f)\end{array}\right\} - n(f, T_0)\alpha\right] \quad \text{[Equation 12]}$$

Here, fitting functions of the phase difference values may be obtained by data-fitting the reference phase difference values $\phi(f)$ and the voltage-on phase difference values $\psi(f)$.

Also, the deviation between the reference phase difference value and the voltage-on phase difference value at a particular frequency $f_o$, i.e., $\phi(f_0)-\psi(f_0)$, is calculated by using the determined fitting functions, and moreover, an electro-optic coefficient value may be calculated by using a refractive index value calculated according to the Sellmeier equation or by using a measured refractive index value.

For determination of a thermo-optic coefficient the thermal expansion coefficient α that is pre-known or measured according to another method is applied to Equation 12.

Here, the Sellmeier equation is well known in the related art, and thus its details thereof are not described.

Figure 8:
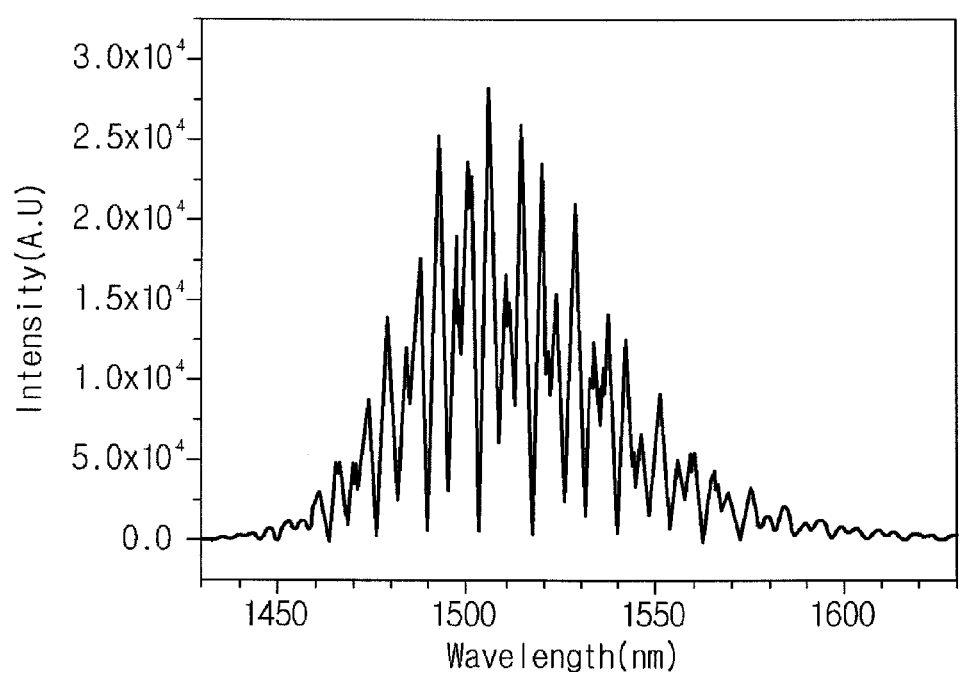
FIG. 8 is a graph showing an interference fringe spectrum measured by using the systems illustrated in FIGS. 1A and 2A.

FIG. 8 is a graph showing the output interference fringe spectrum of an electro-optic sample measured by the system of FIGS. 1A and 2A, wherein dual interference fringes are observed when the optical beam is irradiated onto the optical sample S in an arbitrary polarized direction with respect to the crystal axis of a birefringent optical sample.

A cosine function of a phase in Equation 3 can be expressed according to Equation 13 below.

$$\cos\phi = \frac{I - \{I_A + I_B\}}{2\sqrt{I_A I_B}} \qquad \text{[Equation 13]}$$

Here, $I_A$ and $I_B$ each denote a measured output intensity of an optical beam transmitted through one arm of the interferometer while the other arm is blocked.

Figure 9:
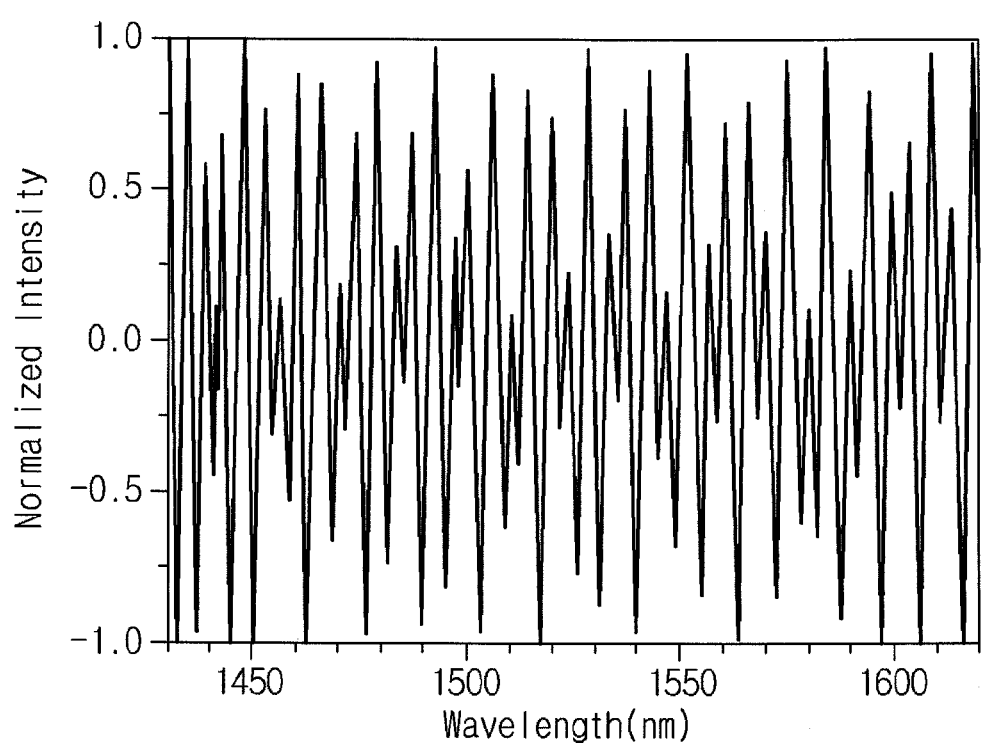
FIG. 9 is a graph showing a normalized pure interference fringe spectrum obtained by subtracting the spectral distribution of the original optical source beam from the interference fringe spectrum of FIG. 8.
Figure 10:
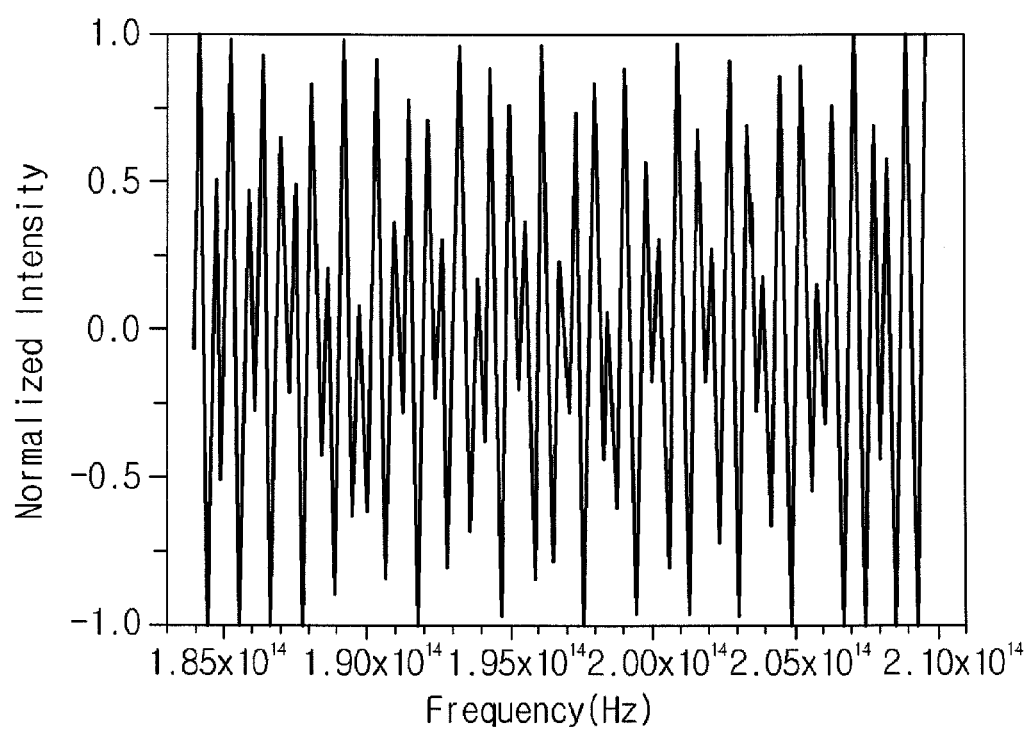
FIG. 10 is a graph showing a pure interference fringe spectrum in the frequency domain, which is obtained by converting the wavelengths of the pure interference fringe spectrum of FIG. 9 into frequencies with the relationship of $f=c/\lambda$ (c: speed of light in a vacuum)

FIG. 9 shows a change curve of the cosine function of Equation 13 as a function of wavelength, which is calculated by using a measured interference fringe output intensity I and the output intensities $I_A$ and $I_B$ of the optical beams transmitted through only one of the two arms with the other arm blocked. FIG. 10 is a graph obtained by converting the wavelength axis of FIG. 8 to a frequency axis by using an equation $$f = \frac{c}{\lambda}.$$

Figure 11:
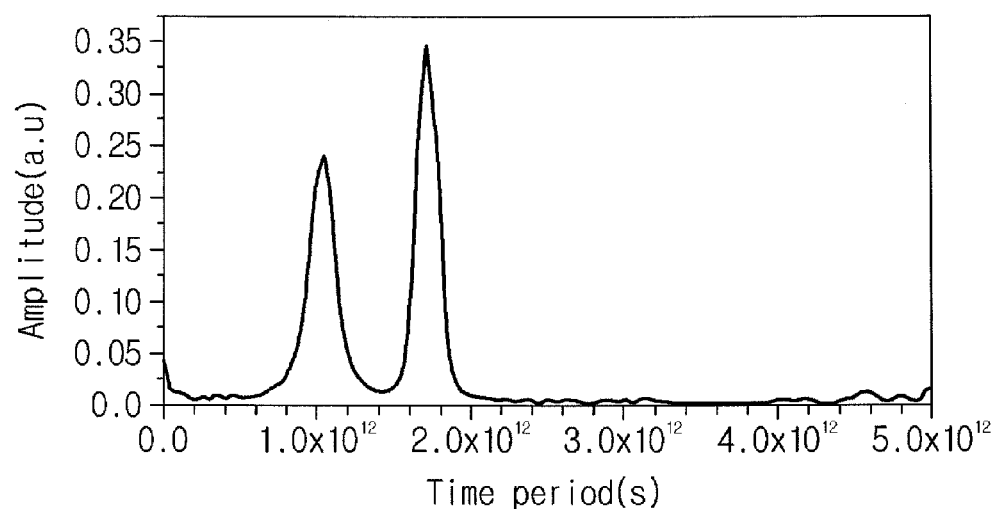
FIG. 11 is a graph showing a result obtained by performing Fourier transform on an interference fringe spectrum obtained from an optical beam irradiated on a birefringent optical sample in an arbitrary polarization direction.

When the optical sample S has a birefringent property and the polarization direction of an input light is irradiated to a direction inducing two polarization components of the birefringence, two vibration periods corresponding to the double interference fringes arose from the birefringence are obtained as shown in FIG. 11, when Fourier transform is performed on the graph of FIG. 10.

One of the Fourier transformed beams is filtered out by using a band-pass filter, and then an inverse Fourier transform is performed on the other beam. Thus, the single interference fringe for each of the birefringent axes can be separated output as shown in FIGS. 12A and 12B.

The polarization of the optical beam irradiated to the optical sample S may be adjusted in such a way that a single interference fringe is shown according to one of the birefringent refractive indices of the optical sample S, by using the polarization controller 122 or 222.

Figure 12A:
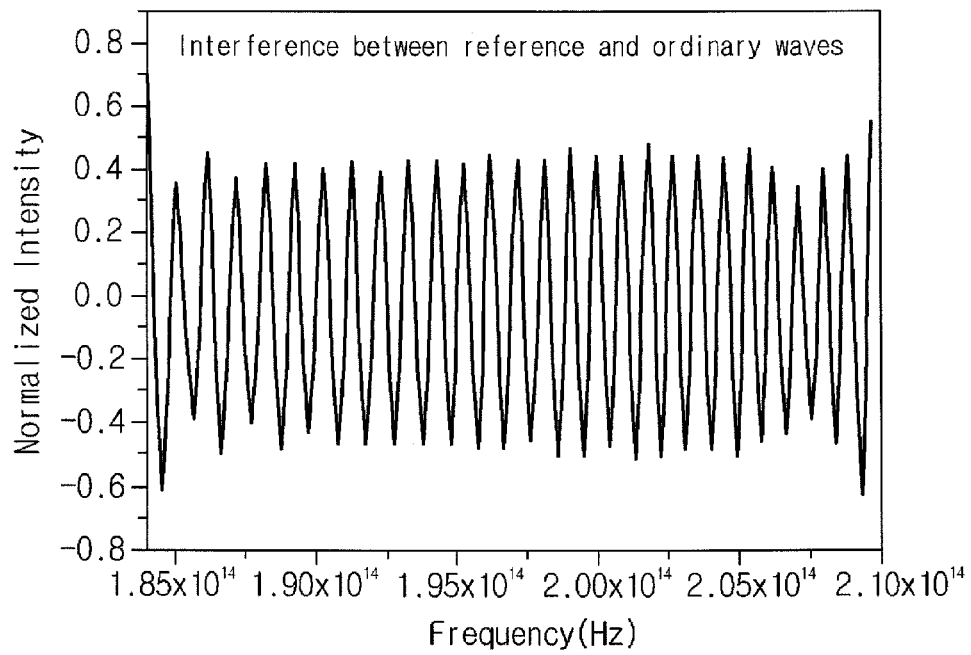
FIGS. 12A and 12B are graphs showing a result obtained by filtering out each of two temporal periods from the graph of FIG. 11, and then by separating out two interference fringes, each for one of the two birefringent polarization directions, with an inverse Fourier transform.
Figure 12B:
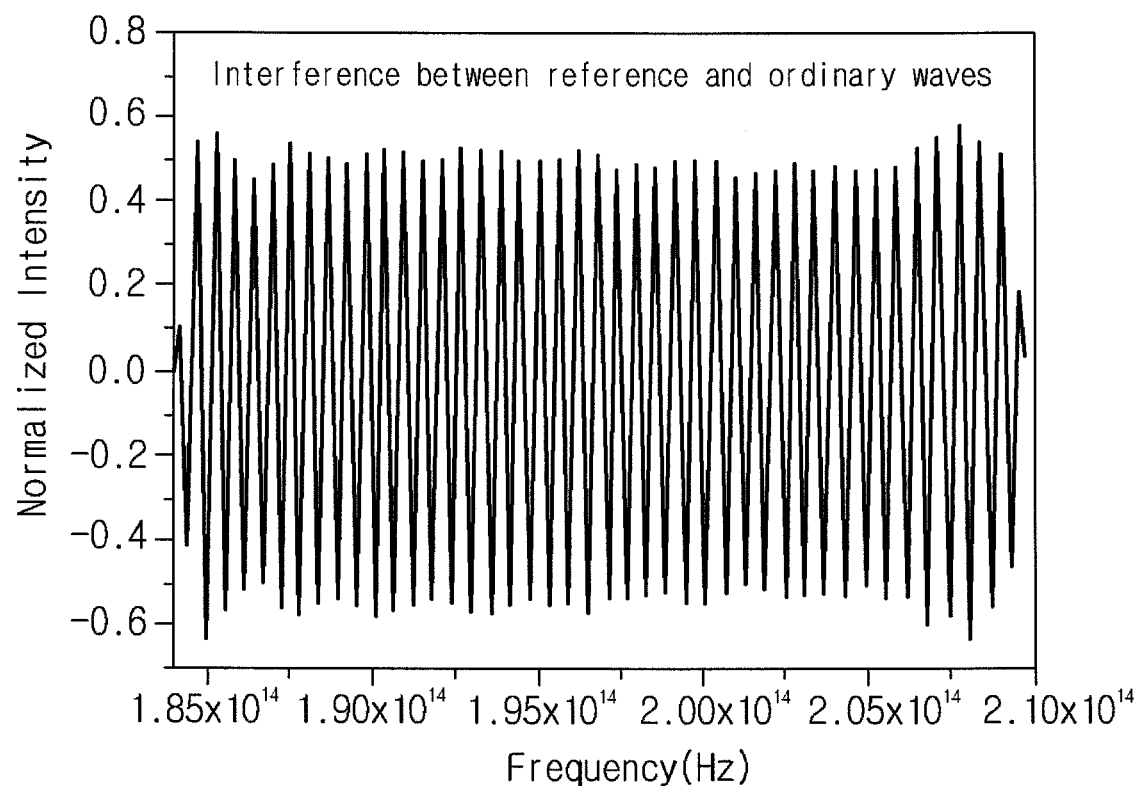

Here, the single interference fringe for each of the birefringent refractive indices is immediately obtained as shown in FIGS. 12A and 12B instead of the double interference fringe of FIG. 10, without performing Fourier transform, filtering, and inverse Fourier transform as described above. Moreover, a single interference fringe of an optical sample that does not have any birefringent property is directly obtained.

Figure 13:
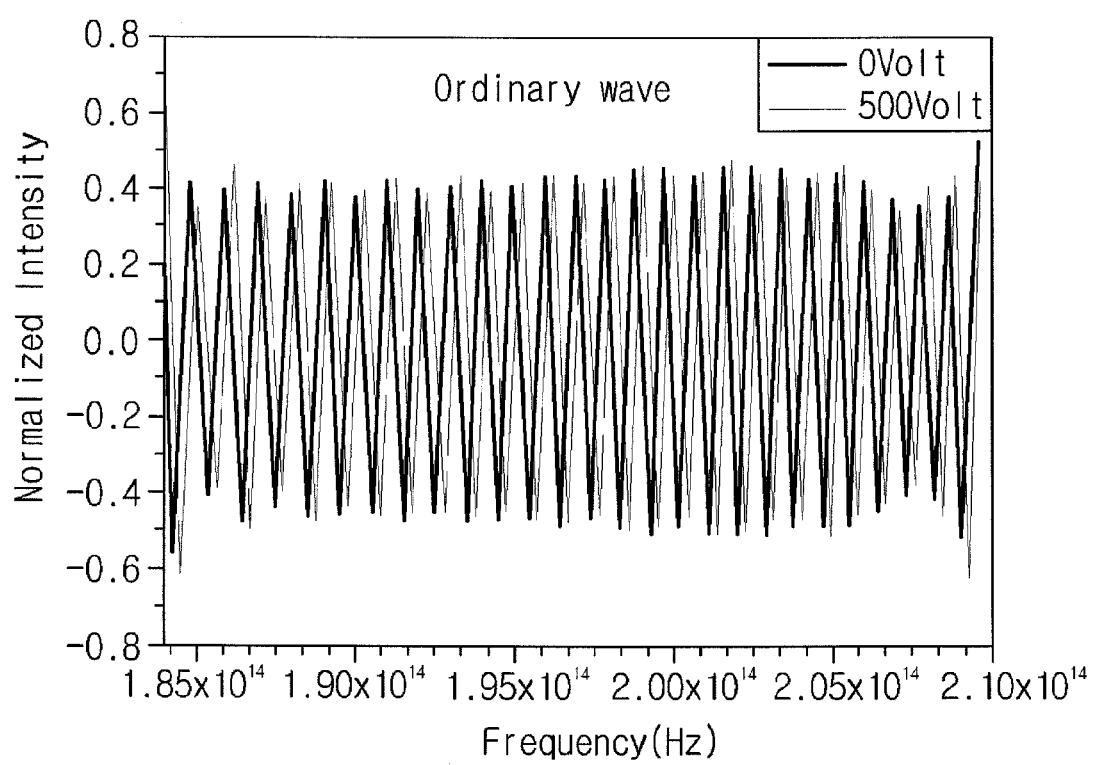
FIG. 13 is a graph showing the phase differences between the interference fringes with no voltage and with a voltage applied to the optical sample.

FIG. 13 is a graph showing phase shifts of the interference fringes for each single refractive index direction between two cases of no electric field and of an electric field applied to the optical sample, like the case of the optical sample having a single refractive index. In the birefringence optical sample, similar phase shifts of an interference fringe for the other refractive index direction are obtained.

Figure 14:
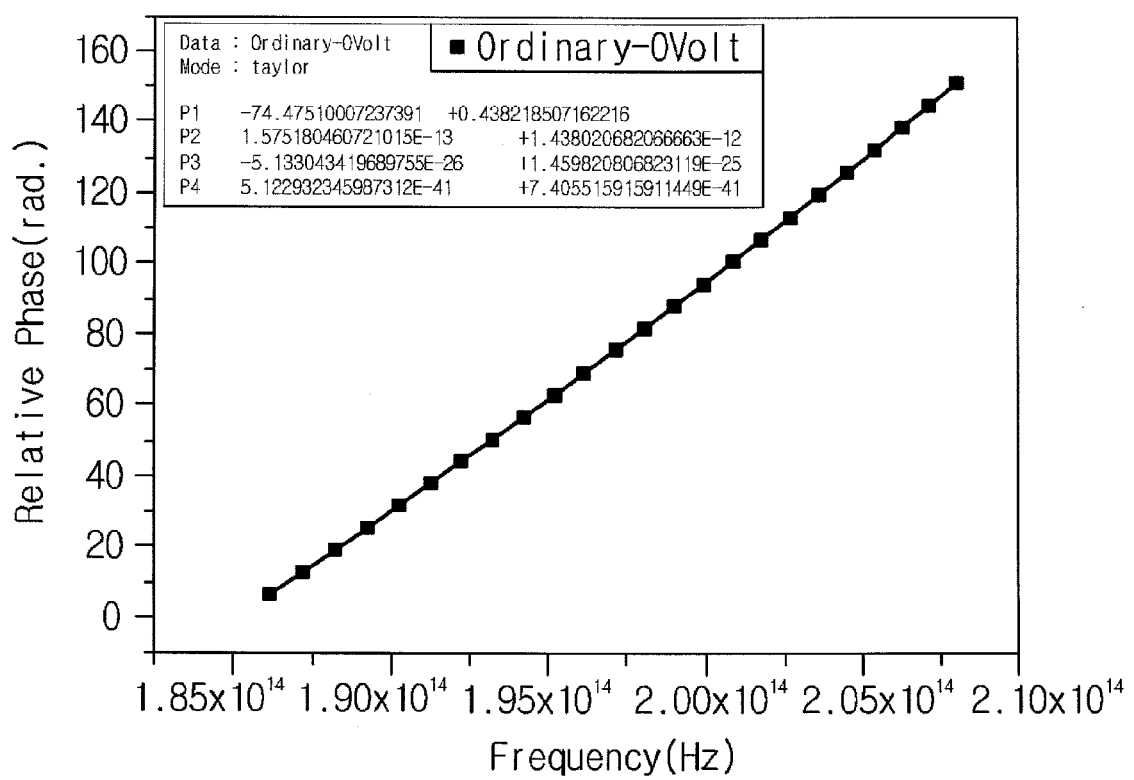
FIG. 14 is a graph showing the phase changes as a function of frequency, calculated by using peak points of an interference fringe spectrum for a single polarization beam corresponding to one of FIGS. 12A and 12B.

Since a phase difference between two adjacent peak points or lowest valley points from each interference fringe of FIG. 12 is 2π, the peak points (or the lowest valley points) of the interference fringe has a phase difference by 2πm according to a degree m of the peak point (or the lowest valley point) separated from a predetermined reference frequency. FIG. 14 is a graph of the phase differences as a function of frequency, and a suitable fitting function may be obtained by data-fitting the plots on the graph. Such a graph of the phase differences as a function of frequency and its fitting function are obtained by performing the same process for each of the interference fringes obtained with no electric field applied and with an electric field applied. An electro-optic coefficient may be calculated according to Equation 11 by using the fitting functions and a known or measured refractive index value of the sample.

A frequency is converted into a wavelength by using an equation $$\lambda = \frac{c}{f},$$

and thus a final electro-optic coefficient as a function of wavelength is obtained.

Figure 15:
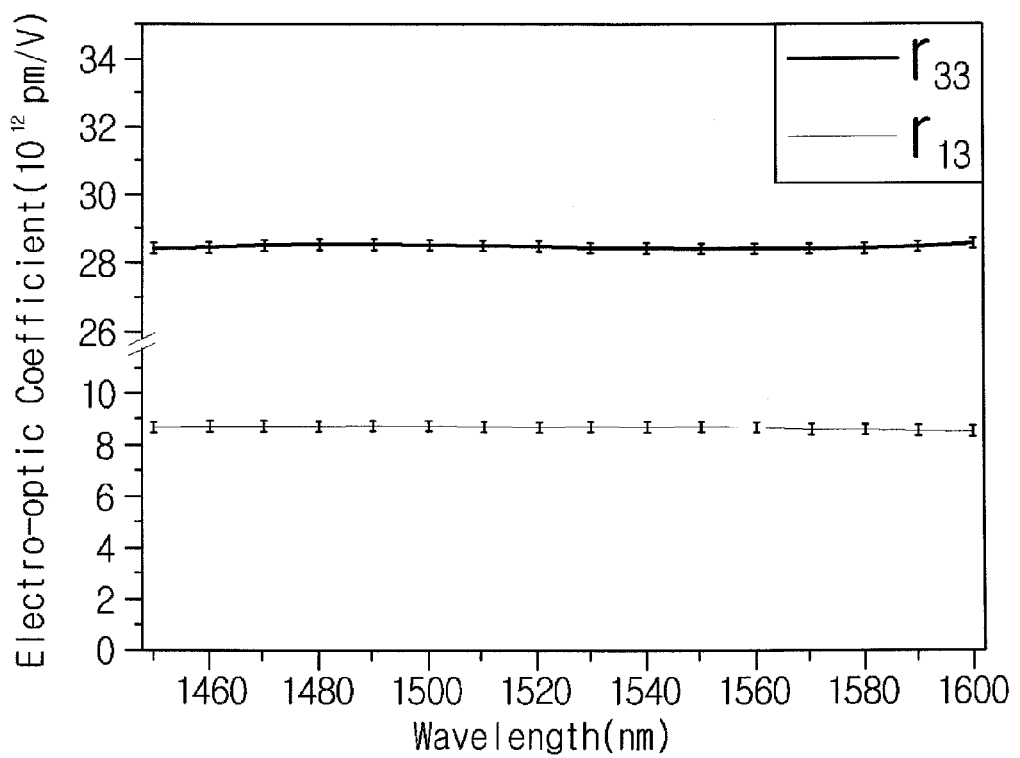
FIG. 15 is a graph showing spectral distributions of the electro-optic coefficients of a birefringent optical sample calculated for each of the birefringent beams from interference fringes and the phase change values, which are measured via a method according to an embodiment of the present invention.

FIG. 15 is a graph showing wavelength dependent electro-optic coefficients of a birefringent optical sample. In the birefringent optical sample, two birefringent electro-optic coefficients can be simultaneously obtained at a single measurement, by adjusting the polarization direction of an optical beam output exiting from the optical connection means 123a to be 45° with respect to the birefringent axis of the birefringent optical sample by using the polarization controller 122 so as to simultaneously show two birefringent characteristics.

In a thermo-optic sample, a single interference fringe as shown in FIG. 12A or 12B is measured unless the thermo-optic sample is a birefringent sample, and when the thermo-optic sample is a birefringent sample, double interference fringes are measured as shown in FIG. 8.

A phase difference function is obtained by calculating phase difference values as a function of frequency by using peak points (or lowest valley points) of an interference fringe while no heat is applied. A phase difference function is also obtained by calculating phase difference values as a function of frequency by using peak points (or lowest valley points) of an interference fringe when the temperature is changed by ΔT with heat applied. Then, a thermo-optic coefficient may be calculated according to Equation 12 by using a refractive index value of a sample and a known or measured thermal expansion coefficient value. The frequency is converted into a wavelength by using an equation $$\lambda = \frac{c}{f},$$

and thus a final thermo-optic coefficients of the sample as a function of wavelength can be obtained.

As described above, an electro-optic coefficient and a thermo-optic coefficient of an electro-optic sample and a thermo-optic sample are accurately measured for each wavelength, respectively.

FIGS. 4A and 4B are diagrams each illustrating the system for measuring an electro-optic coefficient and a thermo-optic coefficient, according to the embodiments of the present invention, wherein the system uses interference fringe measurement. The system is a modified version of the Mach-Zehnder interferometer, but generally is called as a Michelson interferometer. For example, the optical interferometers 300 and 400, i.e., Michelson interferometers, are used by replacing a half of an output terminal of the optical interferometer 100, i.e., a Mach-Zehnder interferometer, of FIGS. 1A and 1B by reflectors 314, 324, 414, and 424, like mirrors, thereby reducing the optical beam transmission lengths of the reference arms 310 and 410, and the sample arms 320 and 420 by half. The input optical path IN and the output optical path OUT, and the reference arms 310 and 410 and the sample arms 320 and 420 are connected to the optical beam dividing and combining units (301 and 401). Here, an optical beam received from the input optical path IN is divided and transmitted to the reference arms 310 and 410, and the sample arms 320 and 420, and optical beams reflected by the reflectors 314, 324, 414, and 424 back to the reference arms 310 and 410, and the sample arms 320 and 420 are combined to output an interfered spectrum into the output optical path OUT.

According to the system, a distance between the optical collimator 312 (the optical beam splitter 401 in FIG. 4B when a bulk optical system is used), and the reflector 314 or 414 is adjusted to achieve a clear interference fringe in the optical spectrum analyzing device 20. Meanwhile, a length of the optical sample S inserted between the optical connection means 323a and the reflector 324 may be half of that of the optical sample S used in FIGS. 1A and 1B.

A method of measuring an electro-optic coefficient or a thermo-optic coefficient of an optical sample, by using interference fringe measurement, wherein the method is performed by the system of FIG. 4A or 4B, is identical to the method using a Mach-Zehnder interferometer described with reference to FIGS. 2A and 2B, and $t_o$ in Equation 1 and 8 may be twice the d/c, i.e., a time taken for a light to proceed the distance d between the optical collimator 312 and the reflector 314, and $L_s$ and $L'_s$ in Equations 2, 4, 6, 8, 9, 10, 11, and 12 may be $2L_s$ and $2L'_s$ so that the electro-optic coefficient or the thermo-optic coefficient is measured in the same manner as in FIG. 1A or 1B.

According to the present invention, the electro-optic coefficient or the thermo-optic coefficient of the optical device and the optical material as a function of frequency may be quickly and accurately measured.

Specifically, external effects on the systems of the present invention are low compared to conventional systems, and moreover, the systems can measure reliable data.

Also, since a pre-prepared reference value is not required, measurement limitation is low compared to conventional technologies, and since a sample is not required to be processed to have a certain shape, the electro-optic or thermo-optic coefficient may be easily and quickly measured.

While the present invention has been particularly shown and described with reference to exemplary embodiments thereof, it will be understood by those of ordinary skill in the art that various changes in form and details may be made therein without departing from the spirit and scope of the present invention as defined by the following claims.

For example, in the above description, structures for measuring an electro-optic coefficient and a thermo-optic coefficient are included in one measuring system, but the present invention is not limited thereto, and a system for measuring an electro-optic coefficient and a system for measuring a thermo-optic coefficient may be individually realized.

What is claimed is:
1. A method of measuring an electro-optic coefficient by using interference fringe measurement, wherein the method is performed by using a system for measuring an electro-optic coefficient by using interference fringe measurement, the system comprising:

a light source for outputting an optical beam of multi-wavelengths;
an optical interferometer comprising:
 an optical beam splitter for dividing the optical beam received from the light source into two separate beams;
 a reference arm for receiving any one of the divided optical beams;
 a sample arm for receiving the other of the divided optical beams and applying a voltage to an optical sample to be measured by being connected to the optical sample; and
 an optical beam combiner for combining and mutually interfering optical beams output through the reference arm and the sample arm; and
an optical spectrum analyzing device for receiving the mutually interfered optical beam from the optical interferometer and analyzing a spectrum of the mutually interfered optical beam, wherein the optical beam splitter and the optical beam combiner are separate from each other,
the method comprising:
obtaining a reference frequency spectrum by measuring a spectrum of the beam penetrated through and output from the interferometer while no voltage is applied to the optical sample, and converting the wavelength to corresponding frequency;
obtaining a reference interference fringe spectrum by normalizing the obtained reference frequency spectrum by excluding the spectral intensity distribution values of the optical beam calculated with a Hilbert transform from the obtained reference frequency spectrum;
calculating reference phase difference values as a function of frequency change from a predetermined reference frequency, by using the obtained reference interference fringe spectrum;
obtaining a voltage-on frequency spectrum by measuring a spectrum penetrated through and output from the optical interferometer while a voltage is applied to the optical sample, and converting the wavelength to a frequency;
obtaining a voltage-on interference fringe spectrum by normalizing the optical beam intensity distribution calculation value according to Hilbert transform excluding from the obtained voltage-on frequency spectrum;
calculating voltage-on phase difference values as a function of frequency change from the predetermined reference frequency, by using the obtained voltage-on interference fringe spectrum;
determining fitting functions for each of the reference phase difference values and the voltage-on phase difference values by data-fitting the reference phase difference values and the voltage-on phase difference values; and
calculating an electro-optic coefficient value by obtaining a reference phase difference value ($\phi(f_0)$) and a voltage-on phase difference value ($\psi(f_0)$) in a predetermined frequency ($f_o$) by using the determined fitting functions, and using a difference ($\phi(f_0)-\psi(f_0)$) between the reference phase difference value ($\phi(f_0)$) and the voltage-on phase difference value ($\psi(f_0)$), and a refractive index value calculated by using a Sellmeier equation or a measured refractive index value.

2. The method of claim 1, further comprising:
before the obtaining of the reference frequency spectrum or the voltage-on frequency spectrum, adjusting an optical beam transmission length of the reference arm in such a way that the spectrum measured by the optical spectrum analyzing device is in a state that shows a relatively clear interference pattern.

3. The method of claim 2, further comprising:

when the optical sample has a birefringence, adjusting polarization of the optical beam irradiated to the optical sample and the optical beam transmission length of the reference arm so that dual interference fringes are measured;

interpolating the reference and voltage-on frequency spectrum data so as to obtain spectra at an equal frequency interval; and classifying interference fringes of an ordinary refracted beam and an extraordinary refracted beam from each of the interpolated reference and voltage-on frequency spectra, by using Fourier transform, filtering, and inverse Fourier transform processes.

\* \* \* \* \*